US011064925B2

(12) United States Patent
Davis

(10) Patent No.: US 11,064,925 B2
(45) Date of Patent: Jul. 20, 2021

(54) JAW EXERCISE SYSTEM AND METHOD OF USING THE SAME

(71) Applicant: Kinesio Designs L.L.C., Newnan, GA (US)

(72) Inventor: Kim Thorsen Davis, Newnan, GA (US)

(73) Assignee: Kinesio Designs L.L.C., Newnan, GA (US)

( * ) Notice: Subject to any disclaimer, the term of this patent is extended or adjusted under 35 U.S.C. 154(b) by 0 days.

(21) Appl. No.: 16/684,276

(22) Filed: Nov. 14, 2019

(65) Prior Publication Data

US 2020/0146609 A1 May 14, 2020

Related U.S. Application Data

(60) Provisional application No. 62/767,370, filed on Nov. 14, 2018.

(51) Int. Cl.
*A61B 5/22* (2006.01)
*A63B 23/03* (2006.01)
(Continued)

(52) U.S. Cl.
CPC ............ *A61B 5/228* (2013.01); *A61C 19/045* (2013.01); *A63B 21/005* (2013.01);
(Continued)

(58) Field of Classification Search
CPC ............... A63B 23/032; A63B 21/021; A63B 2022/0092; A63B 23/03; A63B 21/154;
(Continued)

(56) References Cited

U.S. PATENT DOCUMENTS 3,813,096 A * 5/1974 Welch ................ A63B 21/0004
482/11
5,035,420 A * 7/1991 Beeuwkes, III ..... A63B 23/032
482/11

(Continued)

FOREIGN PATENT DOCUMENTS

KR 10-2004-0018641 A 3/2004

OTHER PUBLICATIONS

International Search Report and Written Opinion for Application No. PCT/US2019/061523 dated Mar. 10, 2020.

*Primary Examiner* — Garrett K Atkinson
(74) *Attorney, Agent, or Firm* — Alston & Bird LLP

(57) ABSTRACT

Various embodiments are directed to systems and methods for evaluating jaw movement characteristics of a user, for example, in a plurality of distinct jaw motion directions. In an example implementation, a jaw exercise system as discussed herein is configured to facilitate the exercise and/or quantification of a user's jaw strength in at least one of six distinct directions. As described herein, the jaw exercise system may comprise a frame assembly to which a user may selectively attach one of a plurality of an interchangeable functional assemblies, each configured to facilitate the evaluation of the jaw movement characteristics of a user in six jaw movement directions. The jaw exercise system comprises one or more of a progressive resistance attachment assembly, a passive motion attachment assembly, a force characterization attachment assembly, and a hyoid motion attachment assembly.

20 Claims, 12 Drawing Sheets

(51) Int. Cl.
*A61C 19/045* (2006.01)
*A63B 21/00* (2006.01)
*A63B 21/062* (2006.01)
*A63B 21/005* (2006.01)

(52) U.S. Cl.
CPC ........ *A63B 21/0622* (2015.10); *A63B 21/154* (2013.01); *A63B 23/03* (2013.01); *A63B 2220/51* (2013.01)

(58) Field of Classification Search
CPC .............. A63B 21/0622; A63B 21/005; A63B 2220/51; A63B 2225/093; A63B 2225/09; A63B 2225/12; A63B 71/0622; A63B 71/023; A63B 2220/80; A63B 2220/833; A61H 23/004; A61H 2201/1604; A61H 2205/02; A61H 2201/165; A61C 19/045; A61C 11/00; A61B 5/228; A61B 2562/0247; A61B 2562/0219; A61B 5/1121; A61B 5/1107; A61B 2505/09; A61B 5/4542; A61B 5/6835; A61B 5/682
See application file for complete search history.

(56) References Cited

U.S. PATENT DOCUMENTS

| | | | |
|---|---|---|---|
| 5,116,359 A | 5/1992 | Moore | |
| 5,158,096 A * | 10/1992 | Clark | A61B 5/107 33/514 |
| 5,374,237 A | 12/1994 | McCarty, Jr. | |
| 5,501,646 A * | 3/1996 | Miller | A63B 23/025 482/10 |
| 5,577,983 A * | 11/1996 | Fraser | A63B 23/032 433/140 |
| 5,582,560 A * | 12/1996 | Magnuson | A63B 23/032 128/861 |
| 5,846,211 A * | 12/1998 | Sakaguchi | A61B 5/228 600/590 |
| 5,899,691 A * | 5/1999 | Parker | A63B 23/032 433/6 |
| 6,050,961 A * | 4/2000 | Arnold | A61B 5/228 600/590 |
| 6,171,214 B1 | 1/2001 | Lundin | |
| 6,179,747 B1 * | 1/2001 | Kelley | A63B 23/025 482/10 |
| 6,361,475 B1 * | 3/2002 | Jobe | A63B 21/0004 482/11 |
| 6,406,404 B1 * | 6/2002 | Chu | A63B 23/032 482/11 |
| 6,413,231 B1 * | 7/2002 | Berman | A61H 1/02 482/11 |
| 6,524,225 B1 * | 2/2003 | Arias | A63B 23/032 482/11 |
| 7,462,132 B2 * | 12/2008 | Kuehne | A63B 23/032 128/861 |
| 7,775,938 B1 * | 8/2010 | Anderson | A61F 5/56 482/11 |
| 7,955,221 B2 * | 6/2011 | Loveday | A63B 23/03 482/10 |
| 8,376,912 B1 * | 2/2013 | Dedvukaj | A63B 21/4025 482/11 |
| 8,702,569 B2 * | 4/2014 | Martin | A63B 21/023 482/11 |
| 9,004,917 B2 * | 4/2015 | Brunner | A61C 19/045 433/69 |
| 9,220,653 B2 * | 12/2015 | Israel | A61H 1/02 |
| 9,227,104 B2 * | 1/2016 | Landis | A63B 21/028 |
| 9,867,753 B2 * | 1/2018 | Garay-Arauz | A61H 1/02 |
| 10,751,152 B2 * | 8/2020 | Cheng | G01S 5/16 |
| 2007/0089752 A1 * | 4/2007 | Christensen, III | A61H 1/0218 128/845 |
| 2013/0157218 A1 * | 6/2013 | Brunner | A61C 19/045 433/69 |
| 2013/0317397 A1 * | 11/2013 | Onno Jan | A61H 1/0218 601/38 |
| 2016/0101315 A1 * | 4/2016 | Garay-Arauz | A61H 1/02 482/11 |
| 2018/0168787 A1 * | 6/2018 | Cheng | H04N 13/239 |
| 2018/0214332 A1 * | 8/2018 | Young | A63B 24/0087 |
| 2019/0290408 A1 * | 9/2019 | Fisker | A61C 13/0004 |

* cited by examiner

JAW EXERCISE SYSTEM AND METHOD OF USING THE SAME

CROSS-REFERENCE TO RELATED APPLICATIONS

This application claims priority to and the benefit of U.S. Provisional Application No. 62/767,370, filed Nov. 14, 2018, entitled "Jaw Exerciser", the contents of which as are incorporated herein in their entirety.

BACKGROUND

Systems and methods have been provided for evaluating jaw movement characteristics of a user in a plurality of jaw motion directions. Jaw movement may be generally understood as comprising use of the temporomandibular joint (TMJ), which provides articulation between the temporal bone of the skull and the condyle of the mandible, with an articular disc located between these bones. Movement at the TMJ during opening and closing of the mouth, as an example, involves both gliding and hinge motions of the mandible. Thus, it should be understood that complex movements in multiple degrees of freedom are involved with jaw movement.

Specifically, the TMJ consists of two (bilateral) modified combined hinge (ginglymoid) and planar (translatory, gliding or arthrodial) synovial joints, each containing an articular disc. Synovial joints are freely moveable joints, as opposed to immovable and slightly moveable joints. Synovial joints are surrounded by an articular capsule, creating a joint cavity between the articulating bones. The capsule has an outer fibrous tissue layer and an inner synovial membrane that secretes synovial fluid. The articulating surfaces of the bones in synovial joints are covered in articular cartilage. This cartilage helps reduce friction between the bones and aids in shock absorption. However, articular cartilage is avascular. Therefore, it is the synovial fluid and not a direct blood supply that, in addition to lubricating the joint, also supplies nutrients, removes metabolic waste products, microbes and debris that arise from normal wear and tear of the joint. When a synovial joint is immobile for any reason, the synovial fluid becomes more viscous leading to a decrease in its production and secretion. This results in a decrease of metabolic activity in the joint, namely a decreased supply of nutrients and a decrease in waste removal. There is an increase production and secretion of synovial fluid with movement of a synovial joint. Thus, movement is beneficial to any synovial joint.

The above-described bilateral TMJ complex notably allows the mandible (chin) the following ranges of motion: elevation (closing mouth), depression (opening mouth), protraction (protrusion, anterior motion/translation, abduction), retraction (retrusion, posterior motion/translation, adduction), left lateral deviation and right lateral deviation (lateral displacement/translation or sideward movement). The muscles involved in elevation of the mandible include the temporalis bilaterally or unilaterally, masseter bilaterally or unilaterally and the left and right medial pterygoids. Because of its bilateral design, it is possible to engage either the right or left elevator muscles independently, as in chewing gum on one side of the mouth. This must be considered when designing any devices configured to exercise the jaw in elevation. The muscles involved in depression of the mandible include the left and right lateral pterygoids, digastric, mylohyoid and geniohyoid. The muscles involved in protraction include the left and right lateral and medial pterygoids bilaterally. The muscles involved in retraction include the temporalis, masseter geniohyoid and digastrics, bilaterally. The muscles involved in left lateral deviation are the left, medial and lateral pterygoids. The muscled involved in right lateral deviation are the right, medial and lateral pterygoids.

Consideration must also be paid to the hyoid bone and its surrounding musculature. The hyoid bone is a small bone located in the anterior neck slightly above the larynx (Adam's apple) approximately level with the tip of the mandible. This bone acts as an attachment site for multiple muscles that depress the TMJ and move the tongue. The digastrics assist with extreme mandibular depression. The mylohyoid and geniohyoid also assist in mandibular depression. Located on the inferior portion of the hyoid is a group of muscles collectively called the infrahyoid muscles whose function is to stabilize and depress the hyoid and aid in yawning and projection of a loud and clear voice. If these muscles are compromised due to disuse, misuse or overuse, they may not be able to provide appropriate support for the superior structures which are involved in jaw movement.

Among other benefits, progressive resistance exercise (weight lifting) has the effect of increasing range of motion of a joint as well as improving the health and function of joint capsules and surrounding soft tissue such as fascia, ligaments, tendons, and muscles. The TMJ, being a synovial joint, is no different in its need for full range of motion exercise. According to the NIH and CDC, there is no effective treatment for TMJ Disorder. However, reviews of the research show that exercise is very promising. Unfortunately, exercise for the TMJ has been neglected by exercise and rehabilitation professionals. Yet research surveys focusing on Tempormandibular Joint Disorders (TMD), state very clearly that of all current interventions, exercise is the only modality that shows promise as an effective treatment for TMD. In fact, there is at least one study showing that exercise is more effective at increasing mandibular depression than splinting, a finding seemingly predictable given what is known regarding the benefits of exercise. However, what continues to slow progress on this front is the lack of ability to standardize, control, measure, and reproduce scientific research. The dearth of focus on the TMJ by exercise and rehabilitation professionals is further evidenced by the following realities: there is no comprehensive equipment to rehabilitate a jaw that has been injured, reconstructed or immobilized, there is no equipment currently available to exercise the muscle of the jaw to prevent injuries, especial in regard to contact sports such as boxing, martial arts, to mention the obvious, there is no equipment currently available to address misalignments of the TMJ due to muscular deficiencies prior to orthodontic care. Additionally, there is a trend to use jaw exercises cosmetically to sculpt facial muscles. However, the equipment that is currently on the market typically focuses on either mandibular elevation or cervical spine flexion, neither of which is a comprehensive or balanced approach to exercise and could exacerbate pain cycles in some individuals. A sound exercise protocol considers the joint and surrounding soft tissue in its full range of motion, not simply its predominant range of motion.

There is thus a need for a progressive resistance jaw exerciser that isolates all six of the muscle groups of the TMJ. Nothing commercially available at this time is comprehensive to this end. Nor does anything offer the ability to standardize, control, measure or reproduce results, an absolute requirement for any scientific research. Until there is equipment and methodology that allows exercise of the jaw to be standardized, controlled, measured and reproduced, there will not be full acceptance from the scientific community on its efficacy.

Indeed, most exercise equipment is designed to improve strength and/or endurance of muscle groups for each joint. The biomechanics of a joint should inform the design of exercise equipment for said joint. The angle of resistance offered by said equipment is most efficient and safe if it aligns with the angle of pull of the muscle groups being isolated. To achieve this, the equipment must isolate one muscle group at a time. There are a variety of ways this is typically accomplished; different equipment must be used for each muscle group, the user must change positions relative to the equipment, the equipment must transform in some way to accommodate the user's stationary position, or some combination of these elements. Further, the concept of progressive resistance is customary for strength improvement. Progressive resistance means that if a muscle is taxed to its strength limits by some sort of a resistance to movement, such as a weight, it will gradually adapt to that weight by growing additional muscle tissue. In order to make further strength gains, the resistance must be increased or strength gains will cease to improve.

Through applied effort, ingenuity, and innovation many deficiencies of such systems have been solved by developing solutions that are in accordance with the embodiments as discussed herein, many examples of which are described in detail herein.

BRIEF SUMMARY

Various embodiments are directed to systems and methods for evaluating jaw movement characteristics of a user in a plurality of jaw motion directions.

Various embodiments relate to a system for evaluating jaw movement characteristics of a user, said user having a jaw, the jaw of the user comprising one or more body parts of a user that are at least substantially functionally attached to said jaw, said system comprising: a frame assembly, the frame assembly comprising: an interchangeable assembly interface; and a stabilizing interface assembly configured to operably secure the frame assembly in an at least substantially stationary position; at least one interchangeable assembly configured to attach to the interchangeable assembly interface of the frame assembly, the at least one interchangeable assembly comprising a plurality of user interface attachments configured to interact with the jaw of the user; wherein the at least one interchangeable assembly further comprises a hexadirectional range of motion such that the respective plurality of user interface attachments of the at least one interchangeable assembly is configured to facilitate the evaluation of a jaw movement characteristic of the user in at least one of six jaw motion directions.

In various embodiments, the at least one of the six jaw motion directions may comprise one or more of a retraction direction, a protraction direction, a left lateral deviation direction, a right lateral deviation direction, an elevation direction and a depression direction. In various embodiments, the at least one interchangeable assembly may comprise a progressive resistance attachment assembly, the progressive resistance attachment assembly comprising: a plurality of user interface attachments configured to interact with the jaw of the user; and a resistance force assembly configured to provide a resistance force in a resistance direction, a directional configuration of the resistance direction being based on a user configuration of the progressive resistance attachment assembly; wherein each of the plurality of user interface attachments of the progressive resistance attachment assembly is configured to receive a force from the jaw of the user in at least one of the six jaw motion directions, the progressive resistance attachment assembly being configurable such that each of the six jaw motion directions are substantially opposite a resistance direction; and wherein the six jaw motion directions define a hexadirectional range of motion of the progressive resistance attachment assembly, such that the system is configured to evaluate a jaw movement characteristic of the user in each of the six jaw motion directions. In various embodiments, the resistance force assembly may comprise a pulley device. In various embodiments, the resistance force assembly may comprise two pulley devices.

In various embodiments, the at least one interchangeable assembly may comprise a passive motion attachment assembly, the passive motion attachment assembly comprising: a plurality of user interface attachments configured to interact with the jaw of the user; and a passive engagement force assembly configured to provide an engagement force in an engagement direction, a directional configuration of the engagement direction being based on a user configuration of the passive motion attachment assembly; wherein each of the plurality of user interface attachments of the passive motion attachment assembly is configured to apply an engagement force to the jaw of the user in at least one of six jaw motion directions, the passive motion attachment assembly being configurable such that each of the six jaw motion directions are substantially similar to an engagement direction.

In various embodiments, the passive engagement force assembly may comprise one or more user control interfaces configured to receive a force applied thereto, the passive engagement force assembly being further configured to transmit the force to at least one portion of the passive motion attachment assembly in an engagement direction. In various embodiments, the passive engagement force assembly may be configured to electronically generate the engagement force.

In various embodiments, the at least one interchangeable assembly may comprise a force characterization attachment assembly configured to attach to the interchangeable assembly interface of the frame assembly, the force characterization attachment assembly comprising: a plurality of user interface attachments configured to receive an applied force transmitted from the user in an applied force direction; the force characterization attachment assembly being configurable such that at least one of six jaw motion directions are substantially similar to an applied force direction; and a force characterization attachment sensor assembly configured to interact with the at least one of the plurality of user interface attachments so as to receive the applied force and measure the magnitude of the applied force in an applied force direction.

In various embodiments, the system may further comprise a hyoid motion attachment assembly configured to attach to the interchangeable assembly interface of the frame assembly and facilitate the evaluation of one or more jaw-related muscles by encouraging user activation thereof and measuring a range of motion of the one or more jaw-related muscles. In various embodiments, the one or more jaw-related muscles may comprise muscles attached to the hyoid bone of the user. In various embodiments, the frame assembly may further comprise a multi-axis attachment interface hinge connected to the interchangeable assembly interface, the multi-axis attachment interface hinge comprising an angular range of motion about a first axis, wherein the multi-axis attachment interface hinge is configured to enable an adjustment of an angular configuration of the interchangeable assembly attached to the interchangeable assembly interface about the first axis. In various embodiments, the first axis may comprise a horizontal axis so as to enable the adjustment of the angular configuration of an interchangeable assembly within a vertical plane, wherein the angular configuration of the of the interchangeable assembly is such that at least one of the six jaw motion directions corresponds to a natural angular motion of the jaw of the user. In various embodiments, the multi-axis attachment interface hinge may further comprise an angular range of motion about a second axis, wherein the multi-axis attachment interface hinge is further configured to enable an adjustment of an angular configuration of the interchangeable assembly attached to the interchangeable assembly interface about the second axis.

In various embodiments, the system may further comprise at least one user stabilization features configured to provide a stationary support for the user such that the user may limit movement of the user as being exclusively movement of the jaw of the user. In various embodiments, the frame assembly may be configured such that an interchangeable assembly configured to attach to the interchangeable assembly interface may be adjustable along both a vertical axis and horizontal axis.

Various embodiments may be directed to a method for evaluating jaw movement characteristics of a user, said user having a jaw, the jaw of the user comprising one or more body parts of a user that are at least substantially functionally attached to said jaw, said method comprising: providing a jaw exercise system comprising: a frame assembly, the frame assembly comprising: an interchangeable assembly interface; and a stabilizing interface assembly configured to operably secure the frame assembly in an at least substantially stationary position; at least one interchangeable assembly configured to attach to the interchangeable assembly interface of the frame assembly, the at least one interchangeable assembly comprising a plurality of user interface attachments configured to interact with the jaw of the user; wherein the at least one interchangeable assembly further comprises a hexadirectional range of motion such that the respective plurality of user interface attachments of the at least one interchangeable assembly is configured to facilitate the evaluation of a jaw movement characteristic of the user in at least one of six jaw motion directions; and interacting with the at least one interchangeable assembly to evaluate a jaw movement characteristic of the user in the at least one of six jaw motion directions.

In various embodiments, the at least one interchangeable assembly may comprise a progressive resistance attachment assembly; and wherein interacting with the at least one interchangeable assembly to evaluate the jaw movement characteristic of the user in the at least one of six jaw motion directions comprises executing at least one active range of motion exercise. In various embodiments, the at least one interchangeable assembly may comprise a passive motion attachment assembly; and wherein interacting with the at least one interchangeable assembly to evaluate the jaw movement characteristic of the user in the at least one of six jaw motion directions may comprise executing at least one passive range of motion exercise. In various embodiments, at least one interchangeable assembly may comprise a force characterization attachment assembly; and wherein interacting with the at least one interchangeable assembly to evaluate the jaw movement characteristic of the user in the at least one of six jaw motion directions may comprise executing jaw force characterization exercise.

Various embodiments are directed to a system for evaluating jaw movement characteristics of a user, said user having a jaw, the jaw of the user comprising one or more body parts of a user that are at least substantially functionally attached to said jaw, said system comprising: a frame assembly, the frame assembly comprising: an interchangeable assembly interface; and a stabilizing interface assembly configured to operably secure the frame assembly in an at least substantially stationary position; a progressive resistance attachment assembly configured to attach to the interchangeable assembly interface of the frame assembly, the progressive resistance attachment assembly comprising: a plurality of user interface attachments configured to interact with the jaw of the user; and a resistance force assembly configured to provide a resistance force in a resistance direction, a directional configuration of the resistance direction being based on a user configuration of the progressive resistance attachment assembly; wherein each of the plurality of user interface attachments of the progressive resistance attachment assembly is configured to receive a force from the jaw of the user in at least one of six jaw motion directions, the progressive resistance attachment assembly being configurable such that each of the six jaw motion directions are substantially opposite a resistance direction; and wherein the six jaw motion directions define a hexadirectional range of motion of the progressive resistance attachment assembly, such that the system is configured to evaluate a jaw movement characteristic of the user in each of the six jaw motion directions.

Various embodiments are directed to a system for evaluating jaw movement characteristics of a user, said user having a jaw, the jaw of the user comprising one or more body parts of a user that are at least substantially functionally attached to said jaw, said system comprising: a frame assembly, the frame assembly comprising: an interchangeable assembly interface; and a stabilizing interface assembly configured to operably secure the frame assembly in an at least substantially stationary position; a passive motion attachment assembly configured to attach to the interchangeable assembly interface of the frame assembly, the passive motion attachment assembly comprising: a plurality of user interface attachments configured to interact with the jaw of the user; and a passive engagement force assembly configured to provide an engagement force in an engagement direction, a directional configuration of the engagement direction being based on a user configuration of the passive motion attachment assembly; wherein each of the plurality of user interface attachments of the passive motion attachment assembly is configured to apply an engagement force to the jaw of the user in at least one of six jaw motion directions, the passive motion attachment assembly being configurable such that each of the six jaw motion directions are substantially similar to an engagement direction; and wherein the six jaw motion directions define a hexadirectional range of motion of the passive motion attachment assembly, such that the system if configured to evaluate a jaw movement characteristic of the user in each of the six jaw motion directions.

A system for evaluating jaw movement characteristics of a user, said user having a jaw, the jaw of the user comprising one or more body parts of a user that are at least substantially functionally attached to said jaw, said system comprising: a frame assembly, the frame assembly comprising: an interchangeable assembly interface; and a stabilizing interface assembly configured to operably secure the frame assembly in an at least substantially stationary position; a force characterization attachment assembly configured to attach to the interchangeable assembly interface of the frame assembly, the force characterization attachment assembly comprising: a plurality of user interface attachments configured to receive an applied force transmitted from the user in an applied force direction; the force characterization attachment assembly being configurable such that at least one of six jaw motion directions are substantially similar to an applied force direction; and a force characterization attachment sensor assembly configured to interact with the at least one of the plurality of user interface attachments so as to receive the applied force and measure the magnitude of the applied force in an applied force direction; wherein the six jaw motion directions define a hexadirectional range of motion of the force characterization attachment assembly, such that the system if configured to evaluate a jaw movement characteristic of the user in each of the six jaw motion directions.

BRIEF DESCRIPTION OF THE DRAWINGS

Reference will now be made to the accompanying drawings, which are not necessarily drawn to scale, and wherein.

DETAILED DESCRIPTION OF VARIOUS EMBODIMENTS

Figure 1:
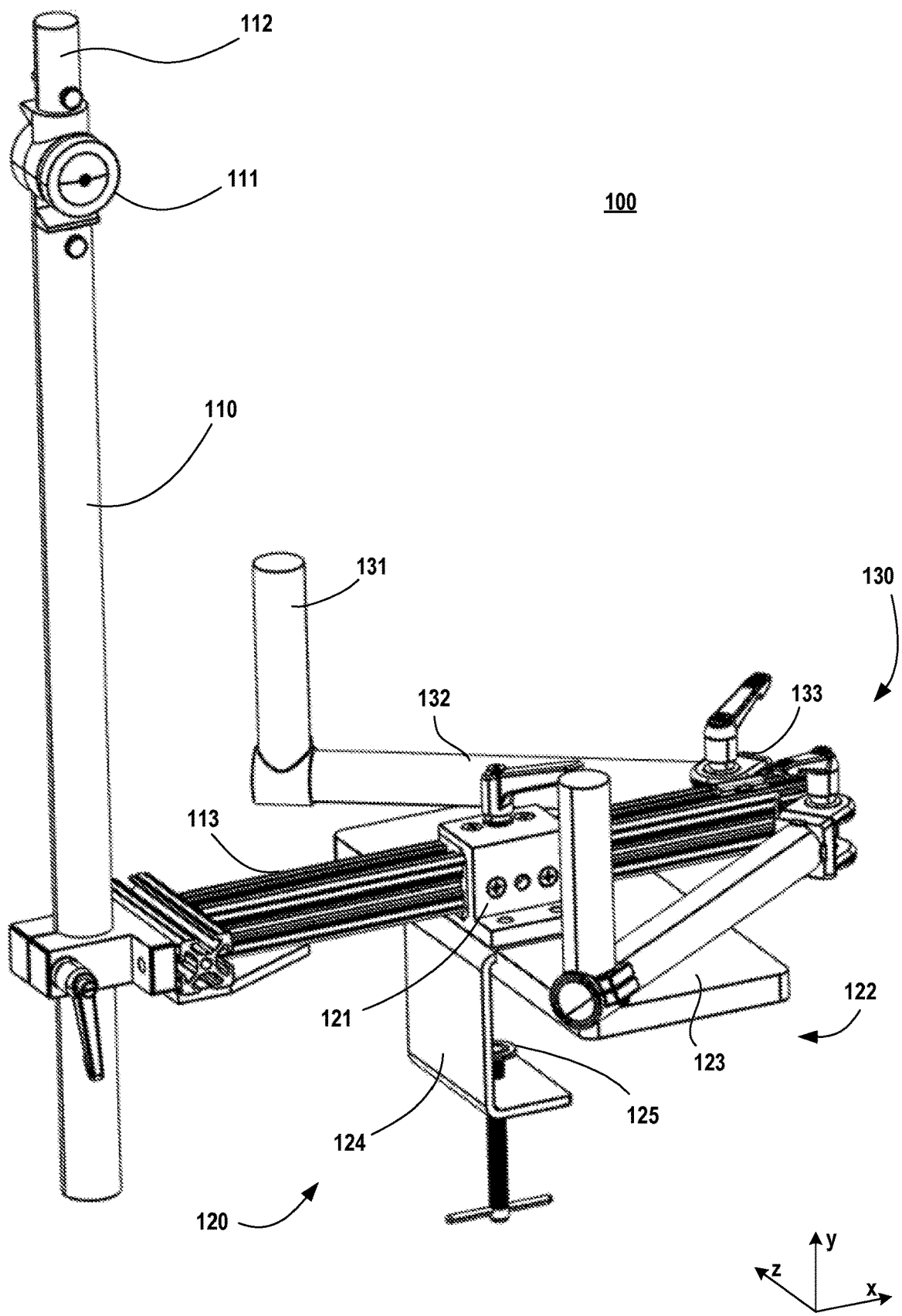
FIG. 1 illustrates a perspective view of an exemplary apparatus according to an embodiment as described herein.

The present disclosure more fully describes various embodiments with reference to the accompanying drawings. It should be understood that some, but not all embodiments are shown and described herein. Indeed, the embodiments may take many different forms, and accordingly this disclosure should not be construed as limited to the embodiments set forth herein. Rather, these embodiments are provided so that this disclosure will satisfy applicable legal requirements. Like numbers refer to like elements throughout.

It should be understood at the outset that although illustrative implementations of one or more aspects are illustrated below, the disclosed assemblies, systems, and methods may be implemented using any number of techniques, whether currently known or not yet in existence. The disclosure should in no way be limited to the illustrative implementations, drawings, and techniques illustrated below, but may be modified within the scope of the appended claims along with their full scope of equivalents. While values for dimensions of various elements are disclosed, the drawings may not be to scale.

The words "example," or "exemplary," when used herein, are intended to mean "serving as an example, instance, or illustration." Any implementation described herein as an "example" or "exemplary embodiment" is not necessarily preferred or advantageous over other implementations.

Overview

Described herein is a system and method for evaluating jaw movement characteristics of a user, for example, in a plurality of distinct jaw motion directions. In an example implementation, a jaw exercise system as discussed herein is configured to facilitate the exercise and/or quantification of a user's jaw strength in at least one of six distinct directions. Such configurations are capable of providing a singular system comprising a small physical footprint that is configured to engage the jaw of a user in a hexadirectional manner so as to flexibly accommodate the needs of a user with respect to directional jaw movement evaluation.

As described herein, the jaw exercise system may comprise a frame assembly to which a user may selectively attach one of a plurality of an interchangeable functional assemblies, each configured to facilitate the evaluation of a user's jaw movement characteristics in six jaw movement directions. As described herein, the hexadirectional movement of a jaw of a user may be embodied as protraction, retraction, lateral displacement in either lateral direction, elevation, and depression. Each of the plurality of an interchangeable functional assemblies may be include various user interface attachments distinctly designed to interact with the jaw of a user and may be selectively arranged by the user about a pivotable connection to the frame to enable the user to interact with the interchangeable functional assembly in each of the aforementioned six jaw movement directions.

Further, as described herein, each of the plurality of interchangeable functional assemblies comprises a unique dynamic functionality such that the system described herein may enable more curated jaw movement exercise that precisely suits the particular needs of a user. For example, the jaw exercise system as described herein comprises a progressive resistance attachment assembly configured to enable active range of motion jaw exercises. In various embodiments, the progressive resistance attachment assembly may allow a user to generate a directional force via the user's jaw and transmit the directional force to a user interface attachment of the progressive resistance attachment assembly in order to overcome a resistance force, such as, for example, a force caused by a weight. In such a configuration, the progressive resistance attachment assembly may effectively allow a user to lift weights with his or her jaw so as to improve and/or quantify jaw strength in each of the aforementioned six jaw movement directions.

Further, the jaw exercise system as described herein comprises a passive motion attachment assembly configured such that the system described herein to enable the execution of passive range of motion jaw exercises. In various embodiments, the passive motion attachment assembly may allow a user to generate a directional engagement force via an independent force generation assembly. A user interface attachment of the passive motion attachment assembly may be configured to receive the generated directional engagement force and transmit it to a user's jaw such that it may displace the jaw in desired direction. For example, the engagement force may be generated by a mechanism that may be moveable along a track in a given direction based on a user's control of, for example, a knob. In such a configuration, the passive motion attachment assembly may effectively allow a user's jaw to remain relaxed while a force is applied thereto so as to improve the flexibility and/or range of motion of the jaw in one or more of the aforementioned six jaw movement directions.

Additionally, the jaw exercise system as described herein comprises a force characterization attachment assembly configured to enable the measurement of the force produced by the jaw of a user in one or more of the aforementioned six jaw movement directions. In various embodiments, the force characterization attachment assembly may allow a user to generate a directional force via the user's jaw and transmit the directional force to a user interface attachment of the progressive resistance attachment assembly in order to engage a force sensor, such as, for example, load cell, which may be configured to measure the magnitude of the directional force generated by the jaw. In such a configuration, the force characterization attachment assembly may effectively allow a user to measure jaw strength so as to quantify and/or track the progression of a user's jaw strength in the six jaw movement directions.

Further, in various embodiments, the system described herein further comprises a hyoid motion attachment assembly configured to facilitate the evaluation of jaw-related muscles, such as, for example, various muscles attached to a hyoid of a user, by encouraging user activation thereof and measuring the range of motion of the muscles.

I. APPARATUS a. Frame Assembly

Figure 2:
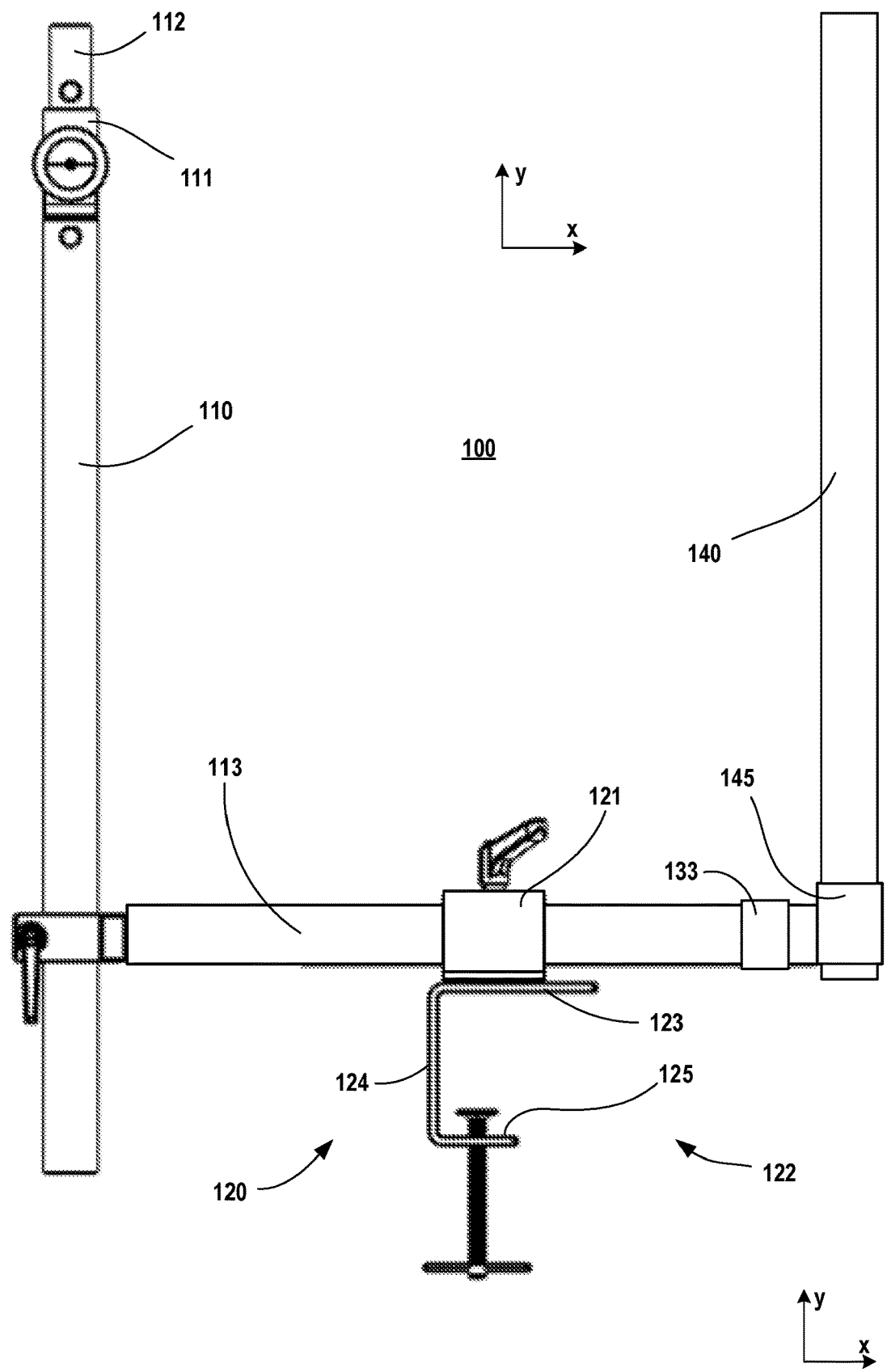
FIG. 2 illustrates a side view of an exemplary apparatus according to an embodiment as described herein.

As illustrated in FIGS. 1-2, the exemplary apparatus described herein may comprise a frame assembly 100. Frame assembly 100 may comprise an interchangeable functional assembly interface 112 configured to engage with an interchangeable functional assembly so as to fixedly secure the interchangeable functionally assembly to the frame assembly 100. For example, an interchangeable functional assembly interface 112 may comprise an attachment stem configured to receive an interface element of an interchangeable functional assembly, as described herein, and secure the interchangeable functional assembly thereto via a pinned connection. Although illustrated in FIG. 1 as comprising an attachment stem configured to engage the interchangeable functional assembly via a pinned connection, it should be understood that the interchangeable functional assembly interface 112 may comprise any mechanism and/or fastening means configured to interact with the interchangeable functional assembly so as to prevent the interchangeable functional assembly from moving relative to the interchangeable functional assembly interface 112.

In various embodiments, the interchangeable functional assembly interface 112 may be operably connected to one or both of a multi-axis attachment interface hinge 111 and a vertical frame attachment arm 110, both of which may be configured to facilitate the adjustability of the positioning of an interchangeable functional assembly attached to the interchangeable functional assembly interface 112. In various embodiments, the multi-axis attachment interface hinge 111 may comprise a hinge element configured to enable the rotation of the interchangeable functional assembly interface 112—and thus an interchangeable functional assembly attached thereto—about a vertical axis. Further, the hinge element may be configured to enable the adjustment of the angular configuration of an interchangeable functional assembly relative to a horizontal plane. In various embodiments, the multi-axis attachment interface hinge 111 may be configured to rotate angularly about a horizontal axis in discrete increments, such that a central vertical axis of the interchangeable functional assembly interface 112 may be angularly configured at, for example, 0, 5, 10, 30, 45, 60, and/or 90 degrees, relative to a horizontal plane.

The multi-axis attachment interface hinge 111 may be connected on one end to a vertical frame attachment arm 110, which may comprise an elongated rigid vertical member configured to enable the adjustment of the vertical positioning of the interchangeable functional assembly interface 112—and thus an interchangeable functional assembly attached thereto—in the y-direction relative to a horizontal frame arm 113 of the frame assembly 100. For example, the vertical frame attachment arm 110 may be adjustable via a clamped support member and/or any other means configured to selectively prevent an interchangeable functional assembly attached to an interchangeable functional assembly interface 112 from being displaced in the y-direction. In various embodiments, the vertical frame attachment arm 110 may be further configured to enable the rotation of the interchangeable functional assembly interface 112—and thus an interchangeable functional assembly attached thereto—about a vertical axis.

The vertical frame attachment arm 110, and/or a support member attached thereto, may be operably connected to a horizontal frame arm 113. In various embodiments, the horizontal frame arm 113 may comprise an elongated rigid horizontal member configured to enable the adjustment of the horizontal positioning of the horizontal frame arm 110—and thus an interchangeable functional assembly operably attached thereto—in the x-direction relative to a stabilizing interface assembly 120 of the frame assembly 100. For example, the horizontal frame arm 113 may be adjustable via a clamped support member and/or any other means configured to stabilize the horizontal frame arm 113 so as to selectively prevent an interchangeable functional assembly operably attached to a vertical frame attachment arm 110 attached thereto from being displaced in the x-direction. As illustrated, the position of the horizontal frame arm 113 along the x-axis may be selectively secured and/or adjusted via the connection of the horizontal frame arm 113 to the horizontal frame arm carriage 121, which may comprise, for example, a user-configured hand brake and may define at least a portion of the stabilizing interface assembly 120. Further, in various embodiments, as described herein, the horizontal frame arm 113 may be configured to be attached to one or both of a handle assembly 130 and a secondary vertical arm assembly 140. In such a circumstance, the horizontal frame arm 113 may be configured to be operably attached to the vertical frame attachment arm 110 at a first end of the horizontal frame arm 113 and to one or both of a handle assembly 130 and a secondary vertical arm assembly 140 at a second end of the horizontal frame arm 113. As described herein, the adjustability of the various elements of the frame assembly 110, such as, for example, the vertical frame attachment arm 110, the multi-axis attachment interface hinge 111, and the horizontal frame arm 113, accommodate a variety of body sizes and adjusts device for optimal use of the at least one interchangeable functional attachments.

In various embodiments, the frame assembly 100 may comprise a stabilizing interface assembly 120 configured to operably secure the frame assembly 100 in an at least substantially stationary position. As described herein, in various embodiments, the stabilizing interface assembly 120 may comprise a horizontal frame arm carriage 121 and a stabilizing interface 122. As described herein, the horizontal frame carriage 121 may function to secure the horizontal frame arm 113 to the stabilizing interface 122 so as to at least partially stabilize the horizontal frame arm 113 and the various apparatus components attached thereto. As shown in FIGS. 1 and 2, the horizontal frame arm carriage 121 may comprise a user-configured hand brake, which may be configured to engage at least a portion of the length of the horizontal frame arm 113 such that the position of the horizontal frame arm 113 along the x-axis may be selectively secured and/or adjusted. In various embodiments, the stabilizing interface assembly 120 may further comprise a stabilizing interface 122. The stabilizing interface 122 may be configured to secure the frame assembly 100 in stable position by anchoring the assembly to an effectively immobilized surface or member. For example, as shown in FIGS. 1 and 2, the stabilizing interface 122 may comprise a clamp configured to secure the frame assembly 100 to an at least substantially flat surface, such as a table, desk, or other substantially immobilized ledge. In various embodiments, the stabilizing interface 122 may comprise an upper stabilizing interface 123, an intermediate stabilizing interface 124, and a lower intermediate stabilizing interface 125. In various embodiments, the upper stabilizing interface 123 may be fixedly secured to the horizontal frame arm carriage 121. Further, in various embodiments, the intermediate stabilizing interface may connect the upper intermediate stabilizing interface 123 and the lower intermediate stabilizing interface 125. For example, the stabilizing interface 122 may be configurable such that an immobilized ledge may be placed in between the upper stabilizing interface 123 and the lower stabilizing interface 125 so as to secure the position of the frame assembly 100 relative to the immobilized ledge. Further, in various embodiments, the lower stabilizing interface 125 may comprise an adjustable element configured to move relative to the upper stabilizing interface 123 in order to adjust to the height of an immobilized ledge so as to further ensure a secure attachment of the frame assembly 100 to the immobilized ledge. As shown in FIGS. 1 and 2, the lower stabilizing interface 125 comprises an adjustable element that may be selectively adjusted to move relative to the upper stabilizing interface 123 using a threaded connection.

In various embodiments, the frame assembly 100 may further comprise a handle assembly 130. A handle assembly 130 may be secured to the horizontal frame arm 113, for example, and may be configured such that it may assist a user interacting with an interchangeable functional attachment in maintaining a correct position by at least partially stabilizing the body of the user. In various embodiments, a handle assembly 130 may comprise a handle 131, a handle arm 132, and a handle arm hinge 133. Further, as shown in FIG. 1, in various embodiments, the frame assembly 100 may comprise more than one handle assemblies (e.g., two handle assemblies). As discussed herein, in various embodiments, each handle assembly 130 may comprise a handle arm hinge 133 that may be secured to the horizontal frame arm 113. For example, the one or more handle arm hinges 133 may be secured to the horizontal frame arm 113 at an end of the horizontal frame arm 113 (e.g., a second end) opposite that which is operably attached to the vertical frame attachment arm 110 (e.g., a first end). A handle arm hinge 133 may comprise a fastening element configured to both operably secure a handle arm 132 connected thereto to the horizontal frame arm 113 and allow for the positional adjustability of the handle arm 132. For example, as shown in FIG. 1, the handle arm hinges 130 may comprise a locking pivot mechanism, which allows for the handle arm hinges 133 to be attached to the horizontal arm frame 113 in a user-configured position along the x-axis, while allowing the handle arms 132 to be adjusted in an angular position relative to the horizontal frame arm 113. In various embodiments, a handle 131 may be fixedly secured to the handle arms 132 to provide a more accessible interface point between a user and each of the one or more handle assemblies 130.

Figure 3:
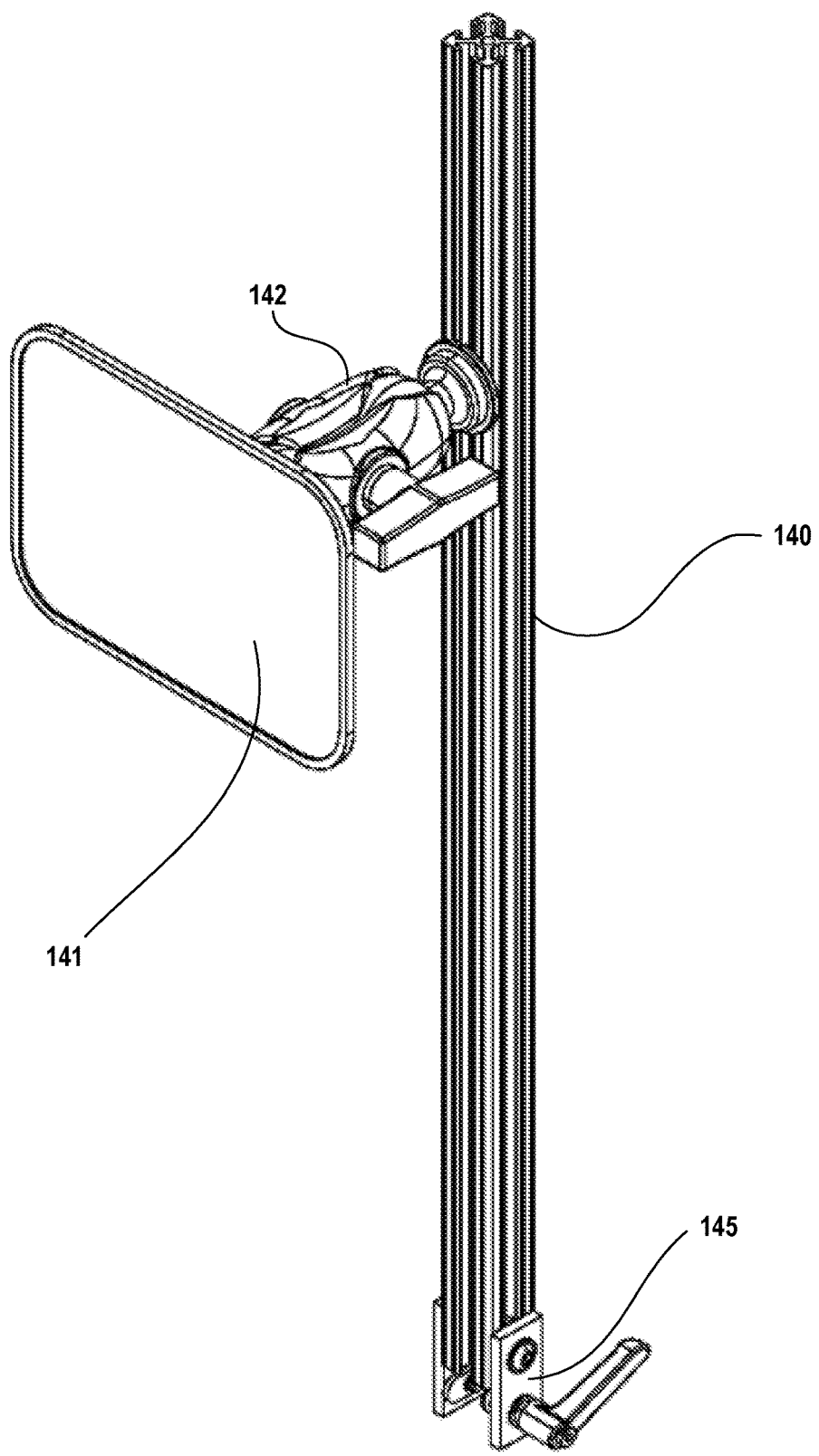
FIG. 3 illustrates a perspective view of an exemplary apparatus according to an embodiment as described herein.
Figure 4:
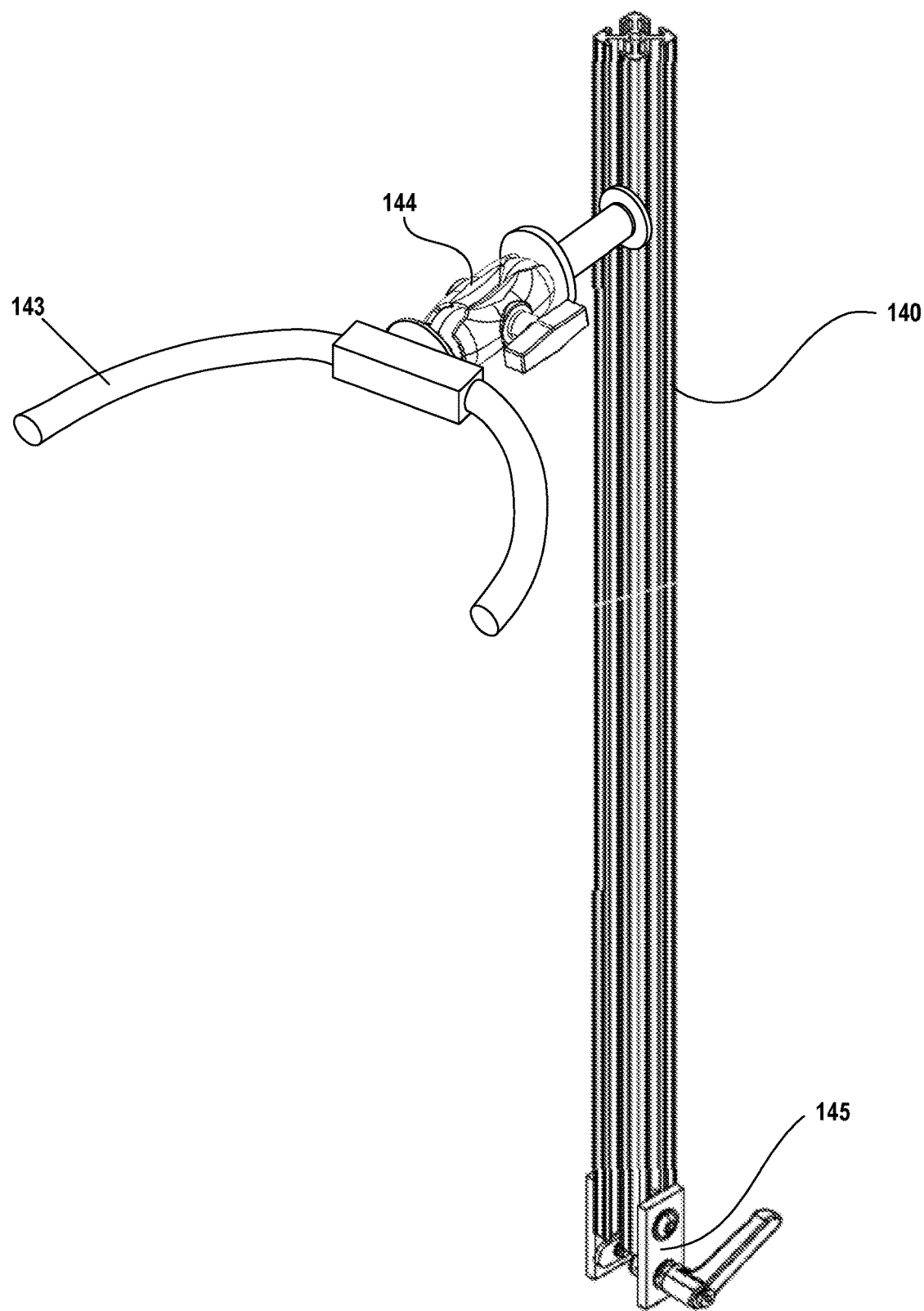
FIG. 4 illustrates a perspective view of an exemplary apparatus according to an embodiment as described herein.

As shown in FIG. 2-4, the frame assembly may further comprise a second vertical arm 140 configured to be secured to the horizontal frame arm 113 at an end of the horizontal frame arm 113 (e.g., a second end) opposite that which is operably attached to the vertical frame attachment arm 110 (e.g., a first end). The second vertical arm 140 may comprise an elongated rigid vertical member positioned along the x-axis and configured to run parallel to the vertical frame axis 110. In various embodiments, the position of the second vertical arm 140 in the y-direction may be configured to be adjustable relative to a horizontal frame arm 113 of the frame assembly 100. The second vertical arm may be operably attached to the horizontal frame arm 113 via a second frame arm attachment element 145, that may be secured to the horizontal frame arm 113. For example, the second frame arm attachment element 145 may comprise a clamped support member and/or any other means configured to selectively stabilize the second vertical arm 140 in a substantially vertical position relative to the horizontal frame arm 113.

As shown in FIGS. 3 and 4, the second vertical arm 140 may be configured to function as a frame to which one or more assembly components may be attached. For example, as illustrated in FIG. 3, the frame assembly 100 may comprise a user reference surface 141, which may be adjustably secured to the second vertical arm 140 via a user reference surface arm 142 attached thereto. In various embodiments, the user reference surface 141 may be embodied as a reflective surface, such as, for example, a mirror, that may be positioned such that when a user is interacting with an interchangeable functional assembly attached to a vertical frame assembly 110, the user may see a reflection of the jaw of the user. Further, the user interface surface 141 may be configured to display an image for use with one or more attachment assemblies as described herein, such as, for example, a hyoid motion attachment assembly. In such a circumstance, for example, the user interface surface 141 may be configured to display an image of a target and/or other locale reference points such that a laser operably attached to a user's neck may appear on the user interface surface 141 and the relative position thereof may be tracked. In various embodiments, the user reference surface arm 142 may be configured to connect the user interface surface 141 to the second vertical arm 140. The user reference surface arm 142 may be positionally adjustable in the y-direction along the vertical axis of the second vertical arm 140. In various embodiments, the length of user reference surface arm 142 may be fully adjustably configurable in three dimensions and/or rotatably such that the user reference surface arm 142 may be configured to arrange the user reference surface 141 in a substantially infinite number of positions.

FIG. 4 illustrates a further non-limiting example embodiment wherein the frame assembly 100 may comprise a head stabilizing interface 143, which may be adjustably secured to the second vertical arm 140 via a head stabilizing arm 144 attached thereto. In various embodiments, the head stabilizing interface 143 may be embodied as a head rest or other adjustable element configured to engage the forehead of a user interacting with an interchangeable functional assembly attached to a vertical frame assembly 110. The head stabilizing interface 143 may define a profile configured to mirror the shape of a forehead so as to facilitate user comfort while stabilizing the head of a user. In various embodiments, the head stabilizing arm 144 may be configured to connect the head stabilizing interface 143 to the second vertical arm 140. The head stabilizing arm 144 may be positionally adjustable in the y-direction along the vertical axis of the second vertical arm 140. In various embodiments, the length of head stabilizing arm 144 may be fully adjustably configurable in three dimensions and/or rotatably such that the head stabilizing arm 144 may be configured to arrange the head stabilizing interface 143 in a substantially infinite number of positions.

b. Progressive Resistance Attachment Assembly

Figure 5:
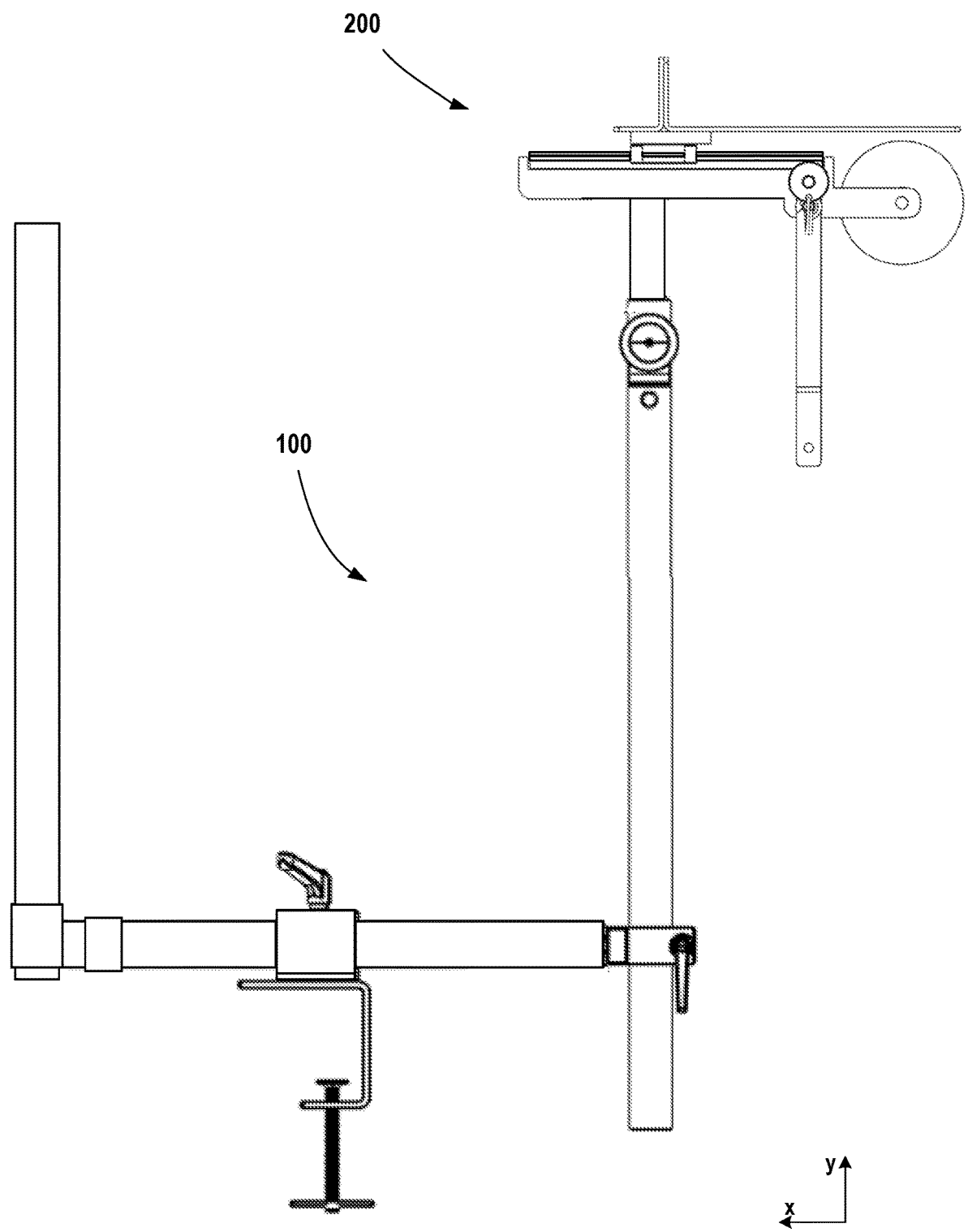
FIG. 5 illustrates a side view of an exemplary apparatus according to an embodiment as described herein.
Figure 6:
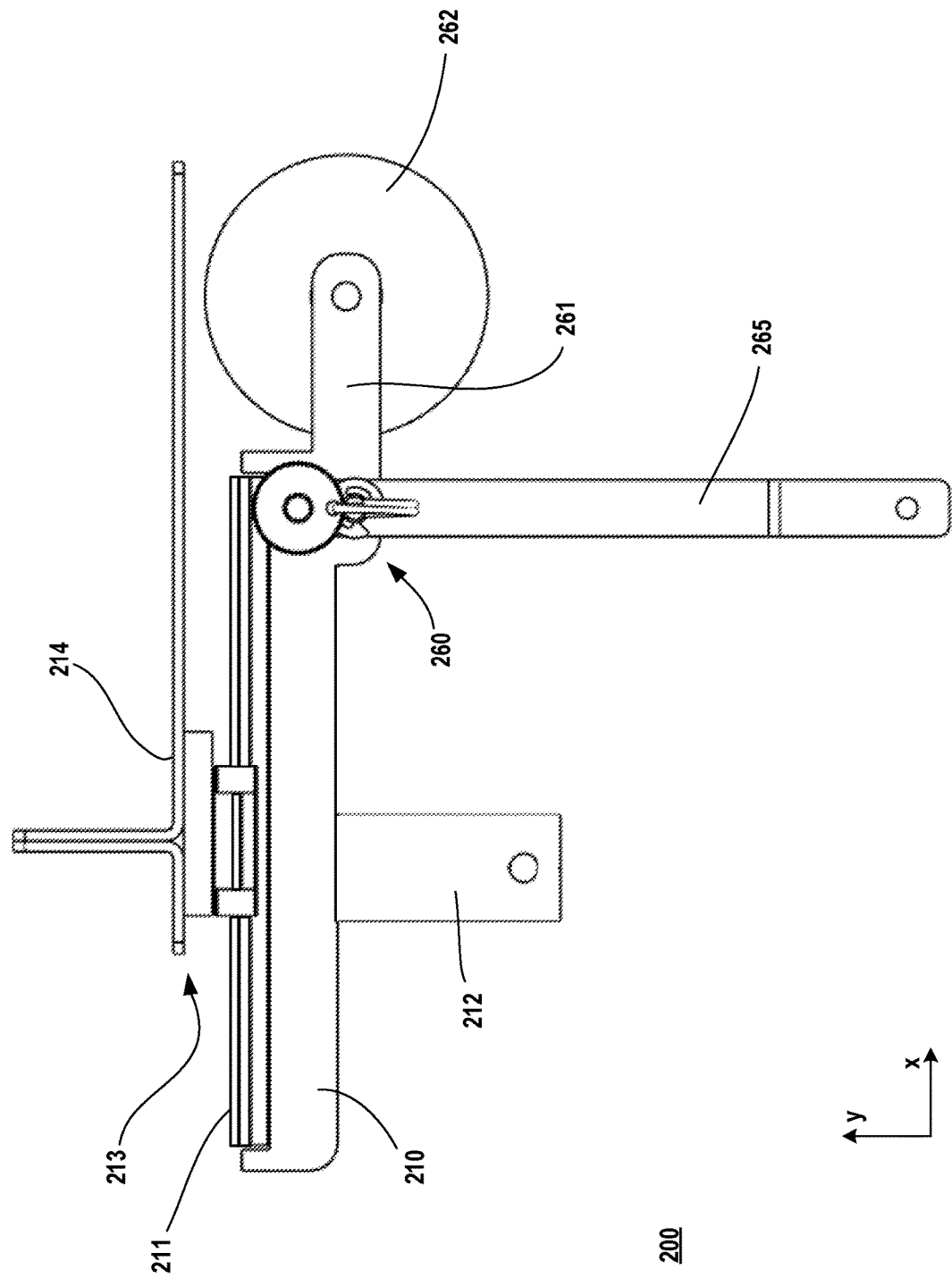
FIG. 6 illustrates a side view of an exemplary apparatus according to an embodiment as described herein.
Figure 7:
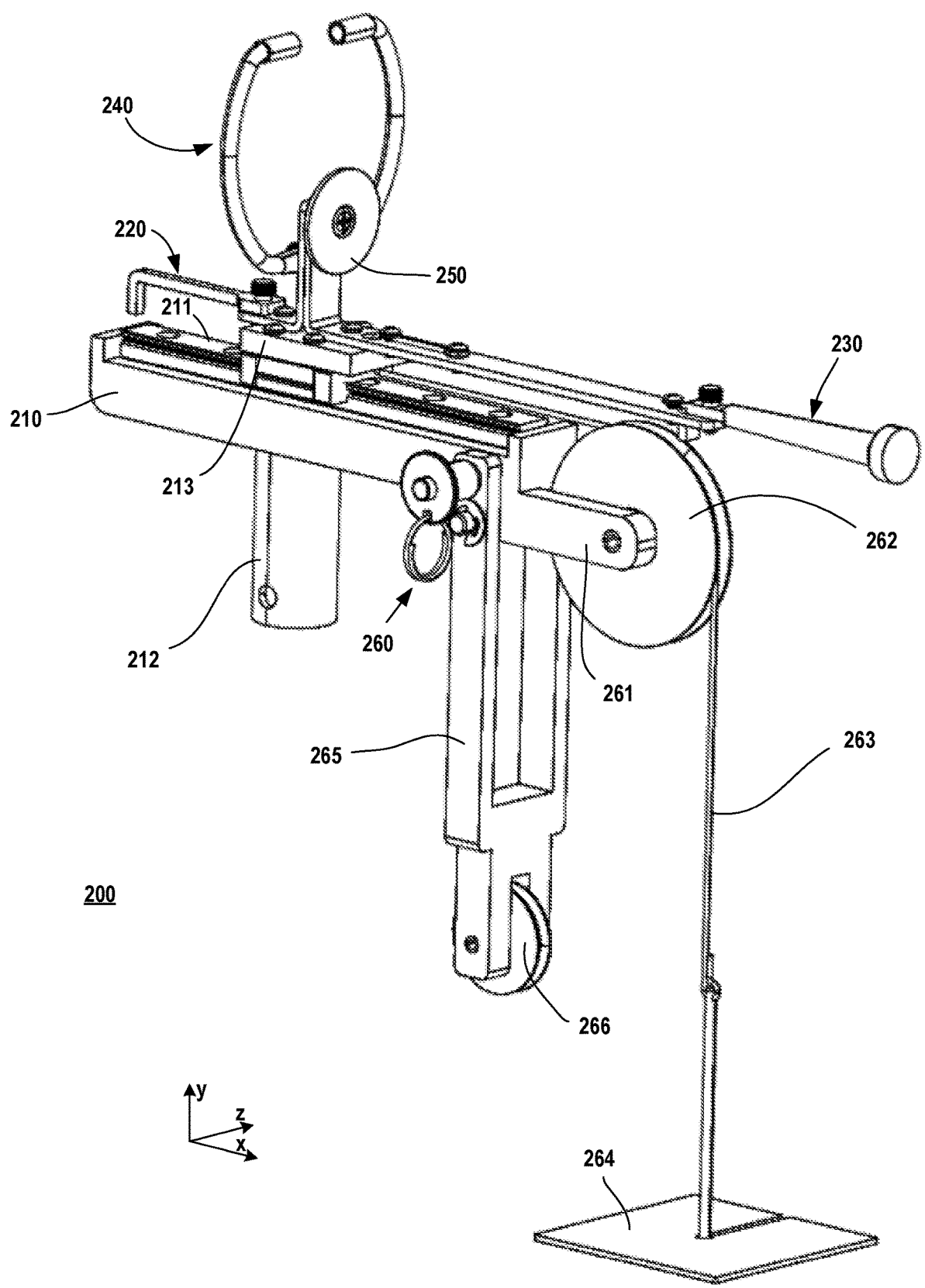
FIG. 7 illustrates a perspective view of an exemplary apparatus according to an embodiment as described herein.
Figure 8B:
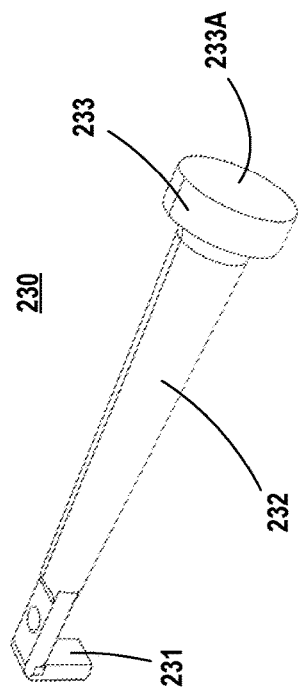
FIGS. 8A-8C illustrate a perspective view of an exemplary apparatus according to an embodiment as described herein.
Figure 8C:
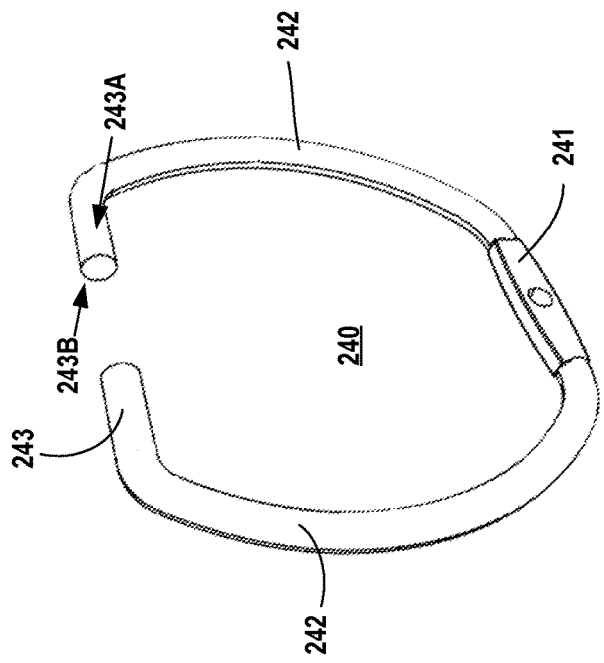
Figure 8A:
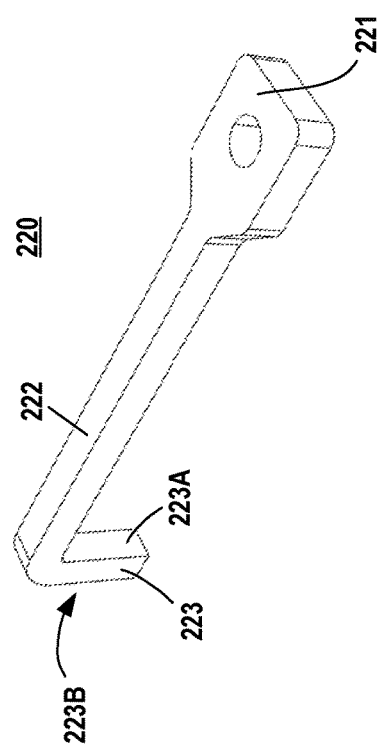

FIGS. 5-7 illustrate an exemplary apparatus according to an embodiment as described herein. In various embodiments, as shown in FIG. 5, an exemplary apparatus as described herein may comprise an interchangeable functional assembly attached to the frame assembly 100. In particular, as shown in FIGS. 5 and 6, an exemplary apparatus may comprise an interchangeable functional assembly, such as, for example, a progressive resistance attachment assembly 200. In various embodiments, a progressive resistance attachment assembly 200 may be configured to facilitate the evaluation of jaw movement characteristics of a user in at least one direction by engaging the jaw of a user (e.g., via a user interface attachment) and operatively applying a known, independently generated resistance force thereto in a resistance direction such that a user may exercise and/or quantify jaw directional strength in the at least one direction (e.g., a direction at least substantially opposite the resistance direction). As described herein, in various embodiments, the progressive resistance attachment assembly 200 may comprise a hexadirectional range of motion such that the progressive resistance attachment assembly 200 may be configurable to evaluate the jaw movement characteristics of a user in each of six directions. For example, the progressive resistance attachment assembly 200 may be configured such that a user may exercise and/or quantify jaw strength via interaction with at least one of a plurality of user interface attachments in at least one of six distinct directions. In various embodiments, the hexadirectional movement of a jaw of a user may be embodied as protraction, retraction, lateral displacement in either lateral direction, elevation, and depression. As described herein, the hexadirectional range of motion of the progressive resistance attachment assembly 200 may be defined by the positive x-direction, the negative x-direction, the positive y-direction, the negative y-direction, the positive z-direction, and the negative z-direction.

In various embodiments, a progressive resistance attachment assembly 200 may comprise a progressive resistance frame attachment interface 212 configured to engage an interchangeable functional assembly interface 112 of an exemplary frame assembly 100 so as to operably secure the progressive resistance attachment assembly 200 to the frame assembly 100. As described above, although illustrated in FIGS. 5 and 6 as engaging the interchangeable functional assembly interface via a pinned connection, it should be understood that the progressive resistance frame attachment interface 212 may comprise any mechanism and/or fastening means configured to interact with the interchangeable functional assembly interface 112 so as to prevent the progressive resistance attachment assembly 200 from moving relative to the interchangeable functional assembly interface 112.

In various embodiments, the progressive resistance attachment assembly 200 comprises a progressive resistance attachment body 210 that is fixedly attached to the progressive resistance frame attachment interface 212. The progressive resistance attachment body 210 may function as a foundational element configured to either directly or indirectly support each of the other components of the progressive resistance attachment assembly 200. In various embodiments, the progressive resistance attachment body 210 may comprise an elongated rigid member extending along a central axis that is perpendicular to the axis along which the progressive resistance frame attachment interface 212 may extend. The progressive resistance attachment body 210 may comprise at least one at least substantially flat surface. In various embodiments, a progressive resistance attachment track 211 may be secured on a substantially flat top surface of the progressive resistance attachment body 210 and configured to extend along an axis parallel to the central axis of the progressive resistance attachment body 210. The progressive resistance attachment track 211 may comprise, for example, a guard rail or other means which may define the range of motion of a progressive resistance attachment carriage 213 engaged therewith. The progressive resistance attachment track 211 may be configured to fit within a portion of a progressive resistance attachment carriage 213 such that the progressive resistance attachment carriage 213 may travel along the progressive resistance attachment track 211 in a travel path that is at least substantially similar to the central axis of the progressive resistance attachment track 211. In various embodiments, the progressive resistance attachment carriage 213 may be connected to the progressive resistance attachment track 211 so as to prevent the progressive resistance attachment carriage 213 from moving relative to the progressive resistance attachment track 211 in any direction other than along an axis parallel to the central axis of the progressive resistance attachment track 211. As shown in FIG. 6, the configuration of the progressive resistance attachment carriage 213 and the progressive resistance attachment track 211 may allow the progressive resistance attachment carriage 213 to smoothly glide along the length of the progressive resistance attachment track 211 in either a positive x-direction or negative x-direction. In various embodiments, for example, the progressive resistance attachment carriage 213 may comprise a ball bearing carriage.

In various embodiments, the progressive resistance attachment carriage 213 may be configured to have a plurality of user interface attachments attached thereto. For example, in various embodiments, the progressive resistance attachment carriage 213 may comprise a progressive resistance attachment carriage user interface mount 214 to which at least one of the user interface attachments may be selectively mounted. In various embodiments, each user interface attachment may be selectively detachable from the progressive resistance attachment assembly 200 (e.g., from the progressive resistance attachment carriage 213). In various embodiments, each of the plurality of user interface attachments may be configured such that a user may exercise and/or quantify jaw strength in one or more directions via interaction therewith. In various embodiments, the hexadirectional movement of the jaw of a user that may occur during interaction with the plurality of user interface attachments may be embodied as protraction, retraction, lateral displacement in either lateral direction, elevation, and depression. For example, each of the plurality of user interface attachments, as described herein, may comprise one or more elements configured to interact with the jaw of a user to facilitate the evaluation of jaw movement characteristics in one or more of the aforementioned six directions.

In various embodiments, as illustrated in FIGS. 7 and 8A-8C, the plurality of user interface attachments may comprise one or more of a retraction attachment 220, a protraction attachment 230, an elevation attachment 240, and a chin pad 250. In various embodiments, retraction attachment 220 may comprise a retraction attachment mount 221, a retraction attachment stem 222, and a retraction attachment interface 223. The retraction attachment mount 221 may be configured to be selectively attached to the progressive resistance attachment carriage 213 via a pinned connection, a nut-and-bolt connection, or any other fastening means configured to prevent the retraction attachment 220 from moving relative to the progressive resistance attachment carriage 213. In various embodiments, the retraction attachment 220 may comprise a retraction attachment stem 222 embodied as an elongated rigid member that extends from the retraction attachment mount 221. In various embodiments, when the retraction attachment 220 is secured to the progressive resistance attachment carriage 213, as described herein, the retraction attachment stem 222 may extend from the retraction attachment mount 221 in a direction at least substantially parallel to the central axis of the progressive resistance attachment track 211. Further, the retraction attachment 220 may comprise a retraction attachment interface 223 positioned at an opposite end of the retraction attachment stem 222 relative to the retraction attachment mount 221. For example, the retraction attachment interface 223 may comprise a flange projecting downward in a direction 90 degrees from the retraction attachment stem 222. The retraction attachment interface 223 may comprise an inner surface 223A and an outer surface 223B positioned facing towards the retraction attachment mount 221 and away from the retraction attachment mount 221, respectively. In various embodiments, the retraction attachment interface 223 may be configured to receive a pulling force from the jaw of a user (e.g., from the inside of the bottom teeth of a user) at the inner surface 223A, wherein the retraction attachment 220 has been arranged so as to be at least partially disposed inside the mouth of the user. For example, as illustrated in FIG. 7, the user may retract the jaw so as to generate a pulling force in the negative x-direction (e.g., the direction away from the retraction attachment mount 221). The retraction attachment 220 may be configured to transmit the force received at the retraction attachment interface 223 to the progressive resistance attachment carriage 213 via the secured connection between the carriage 213 and the retraction attachment mount 221. In such a circumstance, based at least in part on the magnitude of the pulling force received by the retraction attachment 220, the progressive resistance attachment carriage 213 may be configured to move along the progressive resistance attachment track 211 in the direction of the pulling force.

In various embodiments, protraction attachment 230 may comprise a protraction attachment mount 231, a protraction attachment stem 232, and a protraction attachment interface 233. The protraction attachment mount 231 may be configured to be selectively attached to the progressive resistance attachment carriage 213 via a hooked connection, a nut-and-bolt connection, or any other fastening means configured to prevent the protraction attachment 230 from moving relative to the progressive resistance attachment carriage 213. In various embodiments, the protraction attachment 230 may comprise a protraction attachment stem 232 embodied as an elongated rigid member that extends from the protraction attachment mount 231. In various embodiments, when the protraction attachment 230 is secured to the progressive resistance attachment carriage 213, as described herein, the protraction attachment stem 232 may extend from the protraction attachment mount 231 in a direction at least substantially parallel to the central axis of the progressive resistance attachment track 211. Further, the protraction attachment 230 may comprise a protraction attachment interface 233 positioned at an opposite end of the protraction attachment stem 232 relative to the protraction attachment mount 231. For example, the protraction attachment interface 233 may comprise an element positioned at least substantially perpendicular to the central axis of the protraction attachment stem 232 with a surface area configured to receive a pushing force from, for example, the chin of a user. The protraction attachment interface 233 may comprise an outer surface 233A positioned facing away from the protraction attachment mount 231. In various embodiments, the protraction attachment interface 233 may be configured to receive a pushing force from the jaw of a user (e.g., from the chin of a user) at the outer surface 233A, wherein the protraction attachment 230 has been positioned below the mouth and substantially adjacent the front chin of a user. For example, as illustrated in FIG. 7, the user may protract the jaw so as to generate a pushing force in the negative x-direction (e.g., the direction towards the protraction attachment mount 231). The protraction attachment 230 may be configured to transmit the force received at the protraction attachment interface 233 to the progressive resistance attachment carriage 213 via the secured connection between the carriage 213 and the protraction attachment mount 231. In such a circumstance, based at least in part on the magnitude of the pushing force received by the protraction attachment 230, the progressive resistance attachment carriage 213 may be configured to move along the progressive resistance attachment track 211 in the direction of the pushing force.

In various embodiments, elevation attachment 240 may comprise an elevation attachment mount 241, an elevation attachment stem 242, and an elevation attachment interface 243. The elevation attachment mount 241 may be configured to be selectively attached to the progressive resistance attachment carriage 213 via a pinned connection, a nut-and-bolt connection, or any other fastening means configured to prevent the elevation attachment 240 from moving relative to the progressive resistance attachment carriage 213. In various embodiments, the elevation attachment 240 may comprise an elevation attachment stem 242 embodied as an elongated rigid member that extends from the elevation attachment mount 241. As illustrated in FIGS. 7 and 8, in various embodiments, the elevation attachment 240 may comprise two elevation attachment stems 242. As described herein, in various embodiments wherein the elevation attachment 240 includes only a single elevation attachment stem 242, the elevation attachment 240 may be configured to exercise only one lateral side of the jaw of a user at a time. Further, in various embodiments wherein the elevation attachment 240 includes two elevation attachment stems 242, the elevation attachment 240 may be configured to exercise both lateral sides of the jaw of a user at a time. In various embodiments, the one or more elevation attachment stems 242 may be embodied as an elongated rigid members that extend from the elevation attachment mount 241. The one or more elevation attachment stems 242 may comprise a curved configuration so as to isolate the elevation attachment interface(s) 243 while accommodating the curvature of the area proximate the mouth of a user. In various embodiments, when the elevation attachment 240 is secured to the progressive resistance attachment carriage 213, as described herein, the elevation attachment stem(s) 242 may extend from the elevation attachment mount 241 in a direction at least substantially perpendicular to the central axis of the progressive resistance attachment track 211. Further, the elevation attachment 240 may comprise one or more elevation attachment interfaces 243, depending on the number of elevation attachment stem(s) 242 present within the embodiment. The elevation attachment 240 may comprise an elevation attachment interface 243 positioned at an opposite end of each elevation attachment stem 242 relative to the elevation attachment mount 241. For example, each elevation attachment interface 243 may comprise a flange projecting from the corresponding elevation attachment stem 242. Each elevation attachment interface 243 may comprise a lower surface 243A and an upper surface 243B. In various embodiments, the elevation attachment interface 243 may be configured to receive a pushing force from the jaw of a user (e.g., from the top surface of the bottom set of teeth of a user) at the lower surface 243A, wherein the elevation attachment 240 has been arranged so as to be at least partially disposed inside the mouth of the user. For example, as illustrated in FIG. 7 and wherein the apparatus is configured in an elevation exercise configuration, the user may elevate the jaw so as to generate a pushing force in at least generally the positive y-direction (e.g., in a generally upward direction). The elevation attachment 240 may be configured to transmit the force received at the one or more elevation attachment interfaces 243 to the progressive resistance attachment carriage 213 via the secured connection between the carriage 213 and the elevation attachment mount 241. In such a circumstance, based at least in part on the magnitude of the pushing force received by the elevation attachment 240, the progressive resistance attachment carriage 213 may be configured to move along the progressive resistance attachment track 211 in the direction of the pushing force.

In various embodiments, chin pad 250 may comprise an element attached to the progressive resistance attachment carriage 213 (e.g. the progressive resistance attachment carriage user interface mount 214) and positioned at least substantially perpendicular to the central axis of the progressive resistance attachment track 211 with a surface area configured to receive a pushing force from, for example, the bottom and/or one or more sides of the chin of a user. For example, the chin pad 250 may be configured to receive a pushing force from the jaw of a user (e.g., from the side of the chin of the user) upon the user moving the jaw in a lateral direction towards the chin pad 250, wherein chin pad 250 is positioned adjacent the side of the jaw of the user. For example, as illustrated in FIG. 7, the user may move the jaw laterally into the chin pad 250 so as to generate a pushing force in the negative x-direction (e.g., the direction away from the preprimary pulley wheel 262). The chin pad 250 may be configured to transmit the received force to the progressive resistance attachment carriage 213. In such a circumstance, based at least in part on the magnitude of the pushing force received by the chin pad 250, the progressive resistance attachment carriage 213 may be configured to move along the progressive resistance attachment track 211 in the direction of the pushing force. In various embodiments, the progressive resistance attachment assembly 200 may be rotated about the vertical axis of the vertical frame attachment arm 180 degrees, as described herein, such that chin pad 250 may be configured to engage either side of the jaw of a user. Further, in various embodiments, the progressive resistance attachment assembly 200 may be positioned such that the chin pad 250 may engage the bottom of the jaw of a user. In such a circumstance, as described herein, the user may move the jaw at least substantially vertically into the chin pad 250 so as to generate a pushing force that is generally in the negative y-direction (e.g., towards a ground surface).

As described herein, an exemplary progressive resistance attachment carriage 213 may be subjected to a resistance force generated by a resistance force assembly. The resistance force assembly may be configured to apply a resistance force, such as, for example, a pulling force to the progressive resistance attachment carriage 213 in a resistance direction such that the progressive resistance attachment carriage 213 may be predisposed to move along the progressive resistance attachment track 211 in a corresponding direction. As described herein, in various embodiments, the progressive resistance attachment assembly 200 may be configured such that user interaction with one of the plurality of user interface attachments may generate a force in a direction that is at least substantially opposite the resistance direction such that the resistance force may function as force which the user must overcome in order for to move the jaw in the desired direction. Accordingly, the resistance force may embody an adjustable, configurable force that may enable the execution of a strength conditioning exercise for the jaw of a user in a desired direction.

As shown in FIG. 7, a resistance force assembly may comprise a primary pulley arm 261, a primary pulley wheel 262, a resistance rope 263, and one or more weights 264. Further, in various embodiments, a resistance force assembly may further comprise a secondary pulley arm pivot joint 260, a secondary pulley arm 265, and a secondary pulley wheel. In the exemplary embodiment illustrated in FIG. 7, the resistance force may be generated by the one or more weights 264 and the gravitational force associated therewith. The one or more weights 264 may be attached solely to a first end of resistance rope 263—or an attachment piece connected thereto—which may be configured to allow the weight 264 to be suspended, free from external interference, such that the entirety of the force generated by the one or more weights 264 is transferred to the resistance rope 263 in the y-direction. A second end of the resistance rope 263 may be attached to the progressive resistance attachment carriage 213, so as to transfer the resistance force generated by the weights 264 to the progressive resistance attachment carriage 213, and thus, the user interface attachments. In various embodiments, wherein the range of motion of the progressive resistance attachment carriage 213 is limited to the positive and negative x-directions, as described herein, the resistance force assembly may utilize a primary pulley wheel 262 to effectively transfer the resistance force from the y-direction to the x-direction, such that the resistance force generated by the weights 264 may act on the progressive resistance attachment carriage 213. For example, the resistance force may comprise a pulling force experienced by the progressive resistance attachment carriage 213 in the direction of the primary pulley wheel 262. In such a circumstance, the resistance direction may be defined as the positive x-direction (e.g., extending from the progressive resistance attachment carriage 213 towards the primary pulley wheel).

In various embodiments, the primary pulley wheel 262 may be supported by the primary pulley arm 261 such that the primary pulley wheel 262 may only move in a rotational direction about its central axis. The primary pulley wheel 262 may be configured retain at least a portion of the length of the resistance rope 263 therein so as to guide the resistance rope 263 through a 90-degree change of direction. In such a circumstance, the rotational movement of the primary pulley wheel 262 may facilitate the direct transmission of at least substantially all of the resistance force from the weights 264 to the progressive resistance attachment carriage 213. Conversely, upon user interaction with one or more of the user interface attachments, the primary pulley wheel 262 may facilitate the direct transmission of at least substantially all of the counteracting force generated by the user from the progressive resistance attachment carriage 213 to the weights 264. In various embodiments, the primary pulley arm 261 may be embodied a component of the progressive resistance attachment assembly body 210 extending outward in a direction parallel to the central axis of the progressive resistance attachment assembly body 210. The primary pulley arm 261 may be configured to secure the primary pulley wheel 262 in a position about the y-axis that enables a length of the resistance rope 263 extending between the progressive resistance attachment carriage 213 and the primary pulley wheel 262 to be at least substantially parallel with the progressive resistance attachment track 211. Such a configuration of the resistance rope 263 in a singular horizontal plane maximizes the efficiency of the transfer of forces over the primary pulley wheel 262.

As described herein, the progressive resistance attachment assembly 200 may be repositioned in order to effectively configure one or more of the user interface attachments to evaluate jaw movement characteristics in a desired direction. In various embodiments, the resistance force assembly of the progressive resistance attachment assembly 200 may comprise a secondary pulley arm pivot joint 260, a secondary pulley arm 265, and a secondary pulley wheel. The secondary pulley arm 265 may be rotatably fixed to the progressive resistance attachment assembly body 210 about an axis positioned at the secondary pulley arm pivot joint 260. In various embodiments, the secondary pulley arm pivot joint 260 may comprise a pinned connection and/or the like configured to selectively secure the secondary pulley arm 261 in one or more desired rotational directions. In various embodiments, the secondary pulley arm 265 may be rotated between an inactive position, as shown in FIG. 7, wherein the secondary pulley arm 265 is positioned so as not to interfere with one or more of the dynamic components of the apparatus, and an active position, wherein the secondary pulley wheel may be arranged so as to interact with the resistance rope 263 and enable the transfer of the resistance force to a progressive resistance attachment carriage 213 configured to move in a direction other than along the x-axis, as described herein. For example, as described herein, the progressive resistance attachment assembly 200 may be repositioned to a substantially vertical position (e.g., wherein the progressive resistance attachment track 211 extends in a direction 80 degrees relative to the horizontal plane) in order for a user to interact with the elevation user attachment 240. In such a circumstance, the secondary pulley arm 261 and the secondary pulley wheel 262 may be utilized to isolate the travel path of the resistance rope 263 and the weights 264 from the other components of the apparatus while maintaining the transfer of the resistance force to the progressive resistance attachment carriage 213. Although the resistance force assembly described herein comprises weights 264 and one or more pulleys 262, 266, it should be understood that the resistance force assembly may comprise any components configured to generate a resistance force, such as, for example, a spring assembly, a resistance band assembly, and/or the like, that may be operable in the system as described herein.

c. Passive Motion Attachment Assembly

Figure 9:
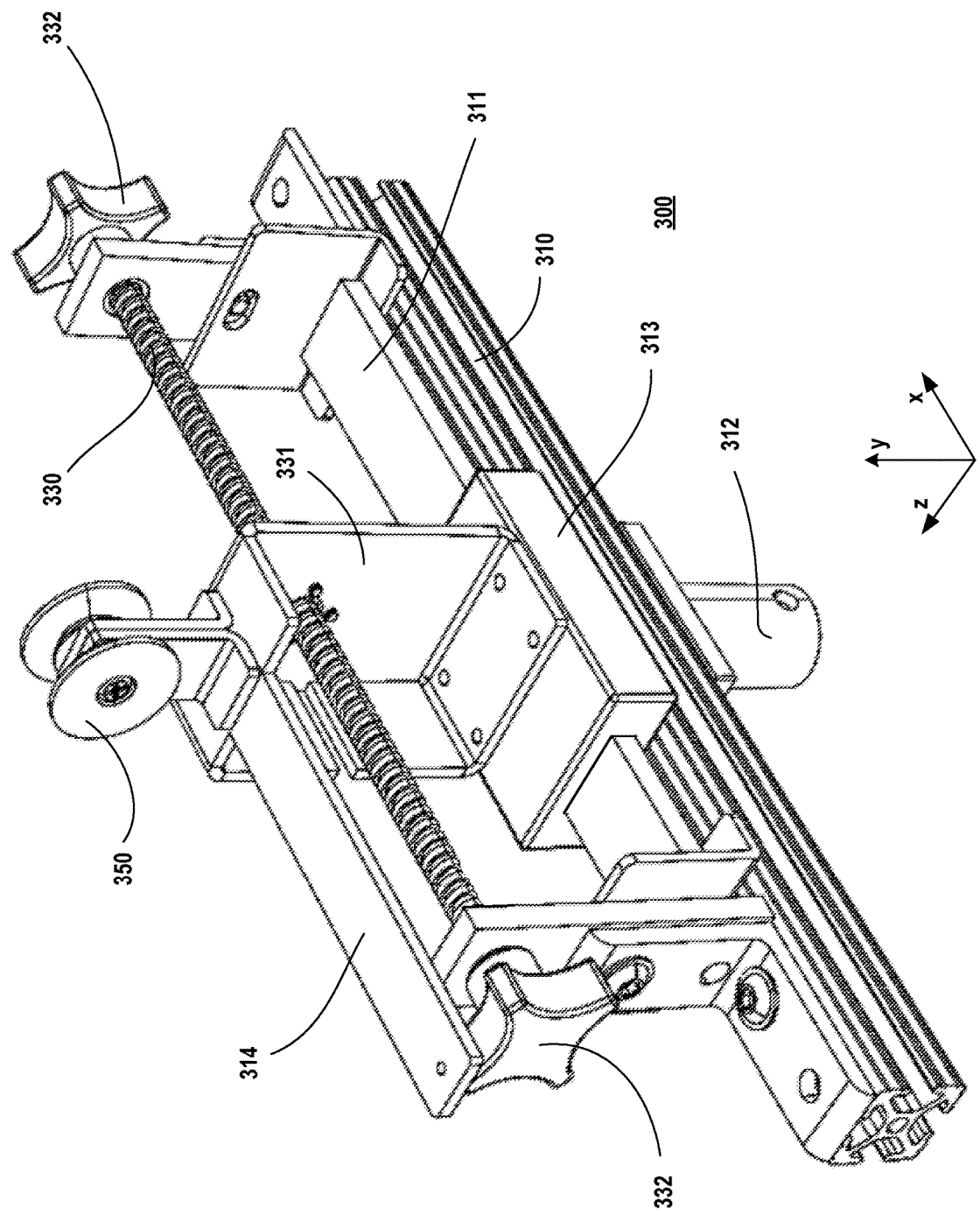
FIG. 9 illustrates a perspective view of an exemplary apparatus according to an embodiment as described herein.
Figure 10:
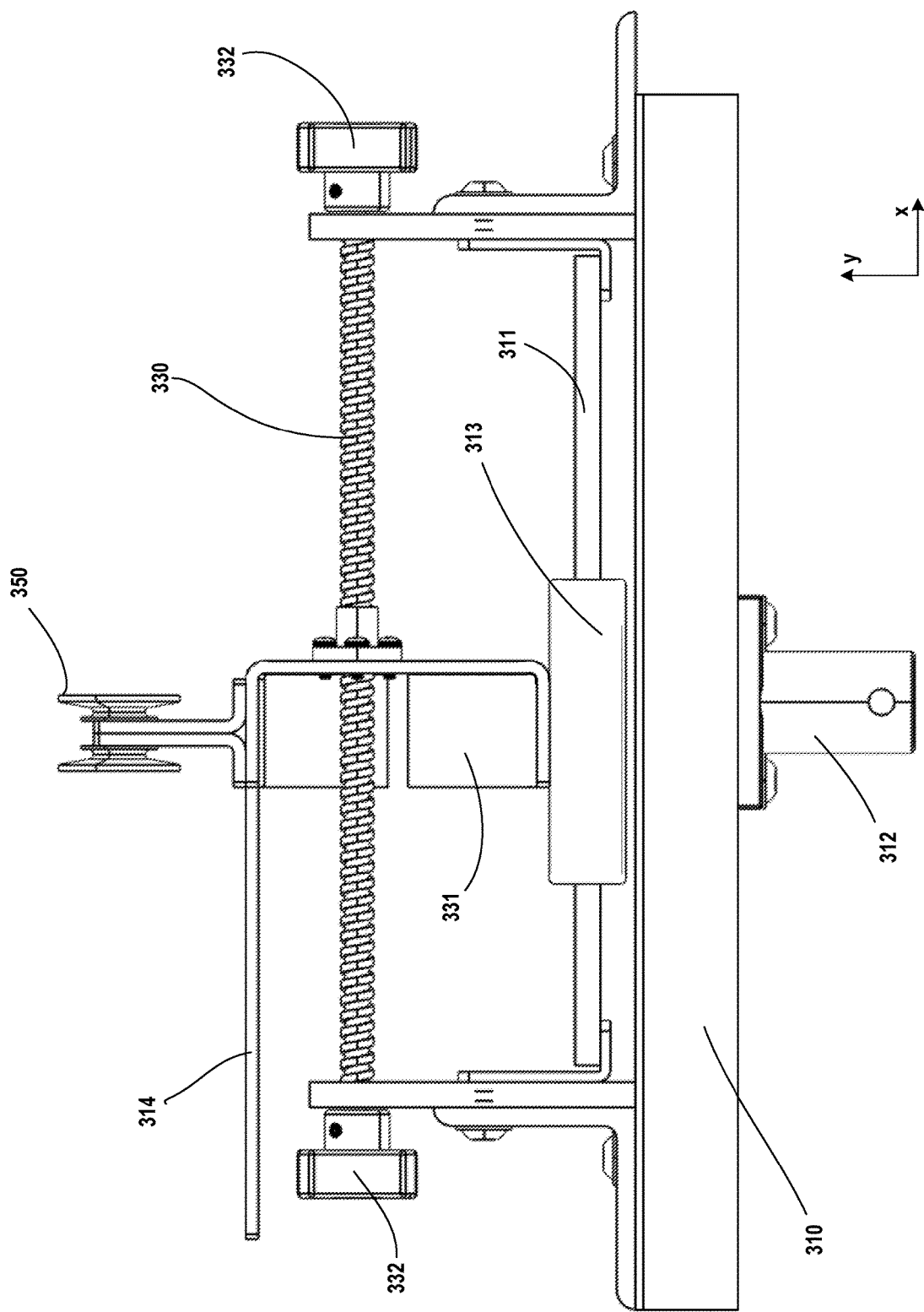
FIG. 10 illustrates a side view of an exemplary apparatus according to an embodiment as described herein.

FIGS. 9-10 illustrate an exemplary apparatus according to an embodiment as described herein. As described herein with respect to FIG. 5, an exemplary apparatus may comprise an interchangeable functional assembly attached to the frame assembly 100. In various embodiments, an exemplary apparatus may comprise an interchangeable functional assembly, such as, for example, a passive motion attachment assembly 300. In various embodiments, a passive motion attachment assembly 300 may be configured to facilitate the evaluation of jaw movement characteristics of a user in at least one direction by engaging the jaw of a user (e.g., via a user interface attachment) and operatively applying a user-generated resistance force thereto in a resistance direction such that a user may exercise (e.g., passively exercise) and/or quantify jaw range of motion in the at least one direction (e.g., a direction at least substantially opposite the resistance direction). As described herein, in various embodiments, the passive motion attachment assembly 300 may comprise a hexadirectional range of motion such that the passive motion attachment assembly 300 may be configurable to evaluate the jaw movement characteristics of a user in each of six directions. For example, the passive motion attachment assembly 300 may be configured such that a user may exercise and/or quantify jaw strength via interaction with at least one of a plurality of user interface attachments in at least one of six distinct directions. In various embodiments, the hexadirectional movement of a jaw of a user may be embodied as protraction, retraction, lateral displacement in either lateral direction, elevation, and depression. As described herein, the hexadirectional range of motion of the passive motion attachment assembly 300 may be defined by the positive x-direction, the negative x-direction, the positive y-direction, the negative y-direction, the positive z-direction, and the negative z-direction.

In various embodiments, a passive motion attachment assembly 300 may comprise a passive motion frame attachment interface 312 configured to engage an interchangeable functional assembly interface 112 of an exemplary frame assembly 100 so as to operably secure the passive motion attachment assembly 300 to the frame assembly 100. As described above, although illustrated in FIGS. 9 and 10 as engaging the interchangeable functional assembly interface via a pinned connection, it should be understood that the passive motion frame attachment interface 312 may comprise any mechanism and/or fastening means configured to interact with the interchangeable functional assembly interface 112 so as to prevent the passive motion attachment assembly 300 from moving relative to the interchangeable functional assembly interface 112.

In various embodiments, the passive motion attachment assembly 300 comprises a passive motion attachment body 310 that is fixedly attached to the passive motion frame attachment interface 312. The passive motion attachment body 310 may function as a foundational element configured to either directly or indirectly support each of the other components of the passive motion attachment assembly 300. In various embodiments, the passive motion attachment body 310 may comprise an elongated rigid member extending along a central axis that is perpendicular to the axis along which the passive motion frame attachment interface 312 may extend. In various embodiments, the passive motion attachment body may comprise two relatively vertical arms extending parallel to one another and in a direction perpendicular to the aforementioned central axis of the passive motion attachment body 310. In various embodiments, the two arms of the passive motion attachment body 310 may be configured to secure the passive engagement force assembly in position, as described herein. Further, the passive motion attachment body 310 may comprise at least one at least substantially flat surface. In various embodiments, a passive motion attachment track 311 may be secured on a substantially flat top surface of the passive motion attachment body 310 and configured to extend along an axis parallel to the central axis of the passive motion attachment body 310. The passive motion attachment track 311 may comprise, for example, a guard rail or other means which may define the range of motion of a passive motion attachment carriage 313 engaged therewith. The passive motion attachment track 311 may be configured to fit within a portion of a passive motion attachment carriage 313 such that the passive motion attachment carriage 313 may travel along the passive motion attachment track 311 in a travel path that is at least substantially similar to the central axis of the passive motion attachment track 311. In various embodiments, the passive motion attachment carriage 313 may be connected to the passive motion attachment track 311 so as to prevent the passive motion attachment carriage 313 from moving relative to the passive motion attachment track 311 in any direction other than along an axis parallel to the central axis of the passive motion attachment track 311. As shown in FIG. 9, the configuration of the passive motion attachment carriage 313 and the passive motion attachment track 311 may allow the passive motion attachment carriage 313 to smoothly glide along the length of the passive motion attachment track 311 in either a positive x-direction or negative x-direction. In various embodiments, for example, the passive motion attachment carriage 313 may comprise a ball bearing carriage.

In various embodiments, the passive motion attachment carriage 313 may be configured to have a plurality of user interface attachments attached thereto. For example, in various embodiments, the passive motion attachment carriage 313 may comprise a passive motion attachment carriage user interface mount 314 to which at least one of the user interface attachments may be selectively mounted. Further, as described herein, the carriage 313 may be operatively connected to the passive motion attachment carriage user interface mount 314 and/or the plurality of user interface attachments via a passive motion attachment guide mount 331, which may be configured to transfer an engagement force generated by a passive engagement force assembly to the passive motion attachment carriage 313. For example, the motion of the passive motion attachment carriage 313 along the passive motion attachment track 311 may be driven by an engagement force.

In various embodiments, each user interface attachment may be selectively detachable from the passive motion attachment assembly 300 (e.g., from the passive motion attachment carriage 313). In various embodiments, each of the plurality of user interface attachments may be configured such that a user may exercise and/or quantify jaw strength in one or more directions via interaction therewith. In various embodiments, the hexadirectional movement of the jaw of a user that may occur during interaction with the plurality of user interface attachments may be embodied as protraction, retraction, lateral displacement in either lateral direction, elevation, and depression. For example, each of the plurality of user interface attachments, as described herein, may comprise one or more elements configured to interact with the jaw of a user to facilitate the evaluation of jaw movement characteristics in one or more of the aforementioned six directions.

In various embodiments, each of the plurality of user interface attachments described above in reference to FIGS. 8A-8C, such as, for example, a retraction attachment 220, a protraction attachment 230, an elevation attachment 240, and a chin pad 250, may be utilized in conjunction with the passive motion attachment assembly 300. In various embodiments, for example, the retraction attachment mount (as shown in FIGS. 7 and 8A-8C) may be configured to be selectively attached to the passive motion attachment carriage 313 via a pinned connection, a nut-and-bolt connection, or any other fastening means configured to prevent the retraction attachment 220 from moving relative to the passive motion attachment carriage 313. In various embodiments, a retraction attachment interface 223 of a retraction attachment 220 may be configured to apply a pulling force to the jaw of a user (e.g., to the inside of the bottom teeth of a user) via an inner surface 223A, wherein the retraction attachment 220 has been arranged so as to be at least partially disposed inside the mouth of the user. For example, wherein the retraction element 220 is attached to the passive motion attachment carriage user interface mount 314 illustrated in FIG. 9, a user may selectively cause the passive motion attachment carriage 313 to move along the passive motion attachment track 311, as described herein, in an engagement direction so as to generate a pulling force in the positive x-direction (e.g., the direction toward the retraction attachment mount 221, when attached to the passive motion attachment carriage user interface mount 314). The retraction attachment 220 may be configured to transmit the force received at the retraction attachment interface 223 to the jaw of a user. In such a circumstance, based at least in part on the magnitude of the pulling force applied to the jaw of the user, the jaw may move in the direction of the pulling force (e.g., in a protraction direction). As used in conjunction with the passive motion assembly 300, the retraction attachment 220 may be used in passive motion exercises to deliberately and forcibly protract the jaw of a user.

Further, in various embodiments, the protraction attachment mount 230 (as shown in FIGS. 7 and 8A-8C) may be configured to be selectively attached to the passive motion attachment carriage 313 via a hooked connection, a nut-and-bolt connection, or any other fastening means configured to prevent the protraction attachment 230 from moving relative to the passive motion attachment carriage 313. In various embodiments, the protraction attachment interface 233 may be configured to apply a pushing force to the jaw of a user (e.g., to the chin of a user) via an outer surface 233A, wherein the protraction attachment 230 has been positioned below the mouth and substantially adjacent the front chin of a user. For example, as illustrated in FIG. 9, a user may selectively cause the passive motion attachment carriage 313 to move along the passive motion attachment track 311, as described herein, in an engagement direction so as to generate a pushing force in the negative x-direction (e.g., the direction away from the protraction attachment mount 231, when attached to the passive motion attachment carriage user interface mount 314). The protraction attachment 230 may be configured to transmit the force received at the protraction attachment interface 233 via the passive motion attachment carriage 313 to the jaw of a user. In such a circumstance, based at least in part on the magnitude of the pushing force applied to the jaw of the user, the jaw may move in the direction of the pushing force (e.g., in a retraction direction). As used in conjunction with the passive motion assembly 300, the protraction attachment 230 may be used in passive motion exercises to deliberately and forcibly retract the jaw of a user.

Further, in various embodiments, the elevation attachment mount (as shown in FIGS. 7 and 8A-8C) may be configured to be selectively attached to the passive motion attachment carriage 313 via a pinned connection, a nut-and-bolt connection, or any other fastening means configured to prevent the elevation attachment 240 from moving relative to the passive motion attachment carriage 313. In various embodiments, the one or more elevation attachment interfaces 243 may be configured to transmit a pulling force to the jaw of a user (e.g., to the top surface of the bottom set of teeth of a user) at the lower surface 243A, wherein the elevation attachment 240 has been arranged so as to be at least partially disposed inside the mouth of the user. For example, as illustrated in FIG. 9 and wherein the apparatus is configured in a depression (i.e. elevation) exercise configuration, a user may selectively cause the passive motion attachment carriage 313 to move along the passive motion attachment track 311, as described herein, in an engagement direction so as to generate a pulling force in the negative y-direction (e.g., in a generally downward direction). The elevation attachment 240 may be configured to transmit the force received at the elevation attachment interface 243 via the passive motion attachment carriage 313 to the jaw of a user. In such a circumstance, based at least in part on the magnitude of the pulling force applied to the jaw of the user, the jaw may move in the direction of the pulling force (e.g., so as to open the mouth of a user). As used in conjunction with the passive motion assembly 300, the elevation attachment 240 may be used in passive motion exercises to deliberately and forcibly depress (i.e. open) the jaw of a user.

In various embodiments, chin pad 350 may comprise an element attached to the passive motion attachment carriage 313 (e.g. the passive motion attachment carriage user interface mount 314). The chin pad 350 may be positioned at least substantially perpendicular to the central axis of the passive motion resistance attachment track 311 with a surface area configured to apply a pushing force to the jaw of a user (e.g., the bottom and/or one or more sides of the chin of a user), wherein chin pad 350 is positioned adjacent the side of the jaw of the user. For example, a user may selectively cause the passive motion attachment carriage 313 to move along the passive motion attachment track 311, as described herein, in an engagement direction so as to generate a pushing force in the positive or negative x-directions (e.g., depending on the direction in which a user displaces the passive motion attachment carriage 313). The chin pad 350 may be configured to transmit the user-generated force received via the passive motion attachment carriage 313 to the jaw of a user. In such a circumstance, based at least in part on the magnitude of the pushing force applied to the jaw of the user, the jaw may move in the direction of the pushing force (e.g., so as to laterally move the jaw of a user). Further, in various embodiments, the passive motion attachment assembly 300 may be positioned such that the chin pad 350 may engage the bottom of the jaw of a user. In such a circumstance, as described herein, a chin pad 350 may be configured to transmit a user-generated force received via the passive motion attachment carriage 313 to the jaw of a user so as to generate a pushing force that is generally in the positive y-direction (e.g., away from a ground surface).

As described herein, an exemplary passive motion attachment carriage 313 (e.g., the passive motion attachment carriage user interface mount 314) may be subjected to receive an engagement force generated by user interaction with a passive engagement force assembly. In various embodiments, user interaction with the passive engagement force assembly may result in the displacement of the passive motion attachment carriage 313 along the passive motion attachment track 311 such that a user interface attachment attached thereto may engage the jaw of a user positioned adjacent the user interface attachment. The engagement force assembly may be configured to apply an engagement force embodied as a driving force to the passive motion attachment carriage 313 in an engagement direction such that the passive motion attachment carriage 313 may be displaced along the passive motion attachment track 311 in a corresponding direction. For example, the distance of the displacement of the passive motion attachment carriage 313 may be proportional to the amount of force applied by a user to the passive motion engagement assembly. As described herein, in various embodiments, the passive motion attachment assembly 300 may be configured such that subsequent user interaction with one of the plurality of user interface attachments may comprise the transmitting of the engagement force to the jaw of the user in the engagement direction via one or more user interface attachments. Accordingly, the engagement force may embody a precise, user-generated driving force that may enable the execution of a passive range of motion exercise for the jaw of a user in a desired direction.

As shown in FIG. 9, the passive motion attachment assembly 300 may comprise a passive engagement force assembly comprising a passive motion attachment guide element 330, the passive motion attachment guide mount 331, and one or more passive motion attachment user control interfaces 332. In various embodiments, the passive motion attachment guide element 330 may comprise an elongated rigid member extending between two arms of the passive motion attachment body 310. The passive motion attachment guide element 330 may be arranged such that the central axis of the passive motion attachment guide element 330 run parallel to the central axis of the passive motion attachment track 311. Further, the passive motion attachment guide element 330 may engage the passive motion attachment guide mount 331 (e.g., by extending therethrough) such that the passive motion attachment guide element 330 may interact with a passive motion attachment carriage 313 that may be operably attached to the passive motion attachment guide mount 331. In various embodiments, the passive engagement assembly may further comprise one or more passive motion attachment user control interfaces 332 connected at one or both ends of the passive motion attachment guide element 330. Each of the one or more passive motion attachment user control interfaces 332 may comprise an interface element configured to facilitate the rotation of the passive motion attachment guide element 330 about its central axis (e.g., via the transfer of a rotational force thereto) such as, for example, a knob, a handle, and/or the like. For example, in various embodiments, the passive motion attachment guide element 330 may comprise a threaded surface such that the passive motion attachment guide element 330 may transmit a driving force to the passive motion attachment guide mount 331 in a lateral direction along the passive motion attachment track 311 in response to receiving a force causing the passive motion attachment guide element 330 to rotate about its central axis. The lateral force exerted on the passive motion attachment guide mount 331 (e.g., in either the positive or negative x-direction) may correspond to the thread direction and the direction of the rotational force received by the passive motion attachment guide element 330. In various embodiments, said lateral force may comprise and/or be at least substantially equal to the engagement force. It should be understood that although the passive engagement force assembly described herein comprises one or more components configured to generate an engagement force manually based on a rotational force received from a user at the one or more passive motion attachment user control interfaces 332, the engagement force may similarly be electronically generated. Further, an electronic sensor device may be utilized with an exemplary passive motion attachment assembly 300 described herein to measure an engagement force, track the lateral displacement of the passive motion attachment carriage 313, and/or the like. For example, said exemplary electronic sensor may be positioned remotely or may physically connected with the passive motion attachment carriage 313, one or more components of the passive engagement force assembly, and/or the like.

d. Force Characterization Attachment Assembly

Figure 11:
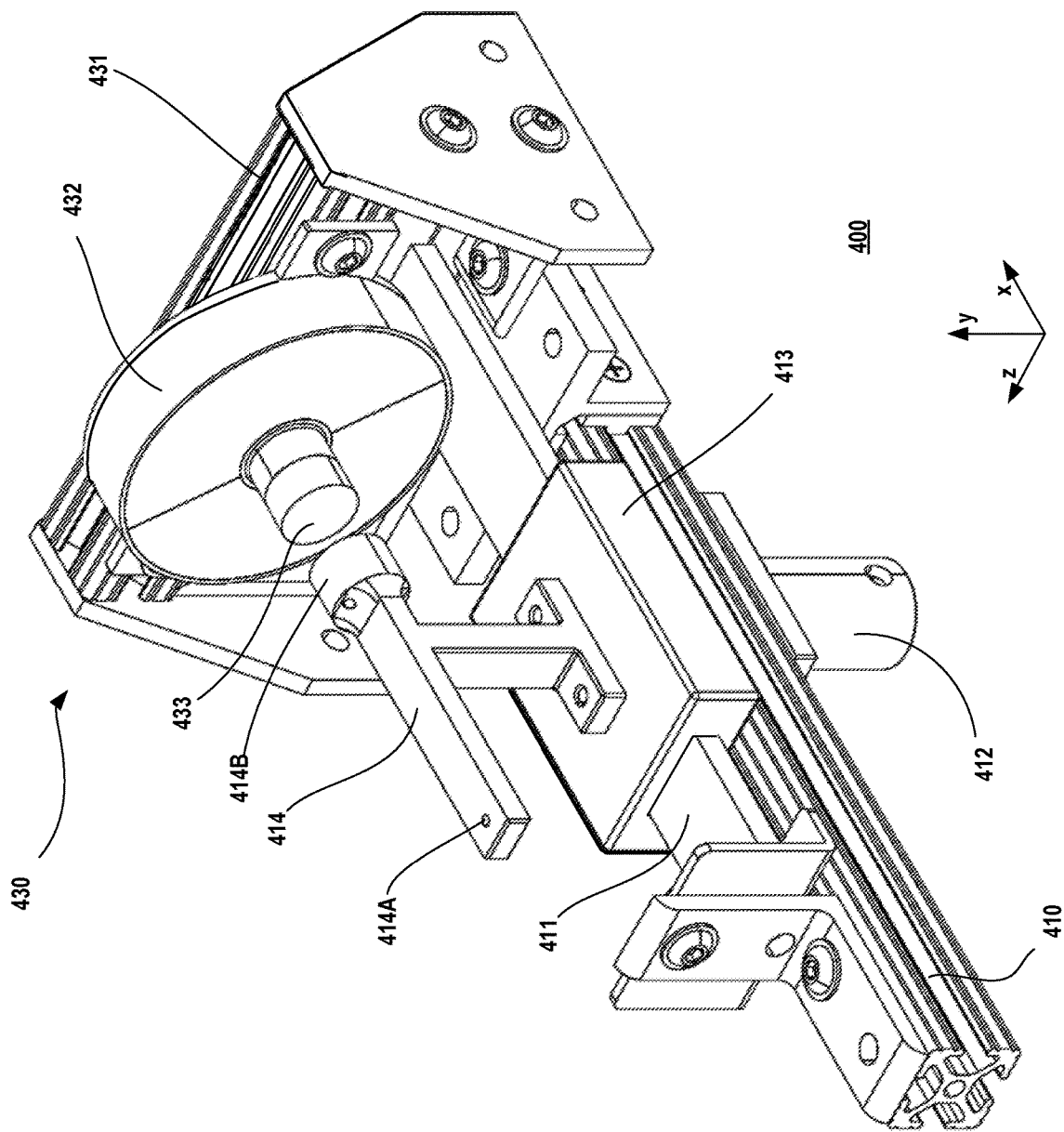
FIG. 11 illustrates a perspective view of an exemplary apparatus according to an embodiment as described herein.

FIG. 11 illustrates an exemplary apparatus according to an embodiment as described herein. As described herein with respect to FIG. 5, an exemplary apparatus may comprise an interchangeable functional assembly attached to the frame assembly 100. In various embodiments, an exemplary apparatus may comprise an interchangeable functional assembly, such as, for example, a force characterization assembly 400. In various embodiments, force characterization assembly 400 may be configured to facilitate the evaluation of jaw movement characteristics of a user in at least one direction by interacting with the jaw of a user (e.g., via a user interface attachment) so as to receive an applied force transmitted from the jaw of a user in at least one of six directions such that the user may quantify jaw strength in the at least one direction. As described herein, in various embodiments, the force characterization assembly 400 may comprise a hexadirectional range of motion such that the force characterization assembly 400 may be configurable to evaluate the jaw movement characteristics of a user in each of six directions. For example, the force characterization assembly 400 may be configured such that a user may quantify jaw strength via interaction with at least one of a plurality of user interface attachments in at least one of six distinct directions. In various embodiments, the hexadirectional movement of a jaw of a user may be embodied as protraction, retraction, lateral displacement in either lateral direction, elevation, and depression. As described herein, the hexadirectional range of motion of the force characterization assembly 400 may be defined by the positive x-direction, the negative x-direction, the positive y-direction, the negative y-direction, the positive z-direction, and the negative z-direction.

In various embodiments, a force characterization assembly 400 may comprise a force characterization frame attachment interface 412 configured to engage an interchangeable functional assembly interface 112 of an exemplary frame assembly 100 so as to operably secure force characterization attachment assembly 400 to the frame assembly 100. As described above, although illustrated in FIG. 11 as engaging the interchangeable functional assembly interface via a pinned connection, it should be understood that the force characterization frame attachment interface 412 may comprise any mechanism and/or fastening means configured to interact with the interchangeable functional assembly interface 112 so as to prevent the force characterization attachment assembly 300 from moving relative to the interchangeable functional assembly interface 112.

In various embodiments, the force characterization attachment assembly 400 comprises a force characterization attachment body 410 that is fixedly attached to the force characterization frame attachment interface 412. The force characterization attachment body 410 may function as a foundational element configured to either directly or indirectly support each of the other components of the force characterization attachment assembly 400. In various embodiments, the force characterization attachment body 410 may comprise an elongated rigid member extending along a central axis that is perpendicular to the axis along which the force characterization frame attachment interface 412 may extend. The force characterization attachment body 410 may comprise at least one at least substantially flat surface. In various embodiments, a force characterization attachment track 411 may be secured on a substantially flat top surface of the force characterization attachment body 410 and configured to extend along an axis parallel to the central axis of the force characterization attachment body 410. The force characterization attachment track 411 may comprise, for example, a guard rail or other means which may define the range of motion of a force characterization attachment carriage 413 engaged therewith. The force characterization attachment track 411 may be configured to fit within a portion of a force characterization attachment carriage 413 such that the force characterization attachment carriage 413 may travel along the force characterization attachment track 411 in a travel path that is at least substantially similar to the central axis of the force characterization attachment track 411.

In various embodiments, the force characterization attachment carriage 413 may be connected to the force characterization attachment track 411 so as to prevent the force characterization attachment carriage 413 from moving relative to the force characterization attachment track 411 in any direction other than along an axis parallel to the central axis of the force characterization attachment track 411. As shown in FIG. 11, the configuration of the force characterization attachment carriage 413 and the force characterization attachment track 411 may allow the force characterization attachment carriage 413 to smoothly glide along the length of the force characterization attachment track 411 in either a positive x-direction or negative x-direction. In various embodiments, for example, the force characterization attachment carriage 413 may comprise a ball bearing carriage. Further, an electronic sensor device may be utilized with the force characterization attachment carriage 413 described herein to measure an engagement force, track the lateral displacement of the force characterization attachment carriage 413, and/or the like. For example, said exemplary electronic sensor may be positioned remotely or may be physically connected with the force characterization attachment carriage 413.

In various embodiments, the force characterization attachment carriage 413 may be configured to have a plurality of user interface attachments attached thereto. For example, in various embodiments, the force characterization attachment carriage 413 may comprise a force characterization attachment carriage user interface mount 414 to which at least one of the user interface attachments may be selectively mounted. In various embodiments, force characterization attachment carriage user interface mount 414 may be attached to a body of the carriage 413 and may comprise a first end 414A and a second end 414B. As described herein, the first end 414A of the force characterization attachment carriage user interface mount 414 may be configured such that at least one of the user interface attachments may be securely fastened thereto. In such a configuration, the first end 414A may be configured to prevent the at least one user interface attachment from moving relative to the force characterization attachment carriage 413. Further, the first end 414A may be configured to receive a force generated by a jaw of a user at the user via the user interface attachment secured thereto. The force characterization attachment carriage user interface mount 414 may be configured so as to transmit the force received at the first end 414A to a second end 414B thereof.

In various embodiments, the second end 414B of the force characterization attachment carriage user interface mount 414 may comprise a substantially flat outer surface positioned facing toward the force characterization attachment sensor interface 433. Alternatively, the second end 414B of the force characterization attachment carriage user interface mount 414 may comprise a hooked element, a plunger element, and/or the like so as to engage the force characterization attachment sensor interface 433 by applying a pulling force thereto. The second end 414B may be positioned such that in response to receiving a force at the first end 414A, the second end 414B may engage at least a portion of a force characterization attachment sensor assembly 430. For example, as shown in FIG. 11, the force characterization attachment carriage 413 may travel along the force characterization attachment track 411 in response to a user-generated jaw force received by the user interface attachment attached to the first end 414. In various embodiments, the range of motion of the force characterization attachment carriage 413 may be configured such that a travel path of the second end 414B of the force characterization attachment carriage user interface mount 414 defines a linear axis that is at least substantially parallel to the central axis of the force characterization attachment track 411 and at least substantially coaxial with a central axis of the force characterization attachment assembly sensor element 432. The second end 414B of the force characterization attachment carriage user interface mount 414 may be positioned such that prior to the force characterization attachment carriage 413 reaching the end of a range of motion about the force characterization attachment track 411 in the positive x-direction (e.g., the direction towards the force characterization attachment sensor assembly 430) the second end 414B may engage the force characterization attachment sensor interface 433. For example, the second end 414B may squarely engage the force characterization attachment sensor interface 433 such that the force is transmitted from the second end 414B in a direction at least substantially perpendicular to the face of the force characterization attachment sensor interface 433. In such a configuration, at least substantially all of the force generated by the jaw of a user and received by a user interface attachment attached to the first end 414A is transmitted through the second end 414B to the force characterization attachment sensor interface 433.

In various embodiments, each user interface attachment may be selectively detachable from the force characterization attachment assembly 400 (e.g., from the force characterization attachment carriage 413). In various embodiments, each of the plurality of user interface attachments may be configured such that a user may quantify jaw strength in one or more directions via interaction therewith. In various embodiments, the hexadirectional movement of the jaw of a user that may occur during interaction with the plurality of user interface attachments may be embodied as protraction, retraction, lateral displacement in either lateral direction, elevation, and depression. For example, each of the plurality of user interface attachments, as described herein, may comprise one or more elements configured to interact with the jaw of a user to facilitate the evaluation of jaw movement characteristics in one or more of the aforementioned six directions.

In various embodiments, each of the plurality of user interface attachments described above in reference to FIGS. 8A-8C, such as, for example, a retraction attachment 220, a protraction attachment 230, an elevation attachment 240, and a chin pad 250, may be utilized in conjunction with the force characterization assembly attachment assembly 400. In various embodiments, for example, the retraction attachment mount (as shown in FIGS. 7 and 8A-8C) may be configured to be selectively attached to the force characterization attachment carriage 414 (e.g., the first end 414A of the force characterization attachment carriage user interface mount 414) via a pinned connection, a nut-and-bolt connection, or any other fastening means configured to prevent the retraction attachment 220 from moving relative to the force characterization attachment carriage 413. As described herein, a retraction attachment interface 223 of a retraction attachment 220 may be configured to receive a pulling force from the jaw of a user (e.g., from the inside of the bottom teeth of a user) at the inner surface 223A, wherein the retraction attachment 220 has been arranged so as to be at least partially disposed inside the mouth of the user. For example, wherein the retraction element 220 is attached to the force characterization attachment carriage user interface mount 414 illustrated in FIG. 11, a user may retract the jaw so as to generate a pulling force in the negative x-direction (e.g., the direction away from the force characterization attachment sensor assembly 430). The retraction attachment 220 may be configured to transmit the force received at the retraction attachment interface 223 to the force characterization attachment carriage 413 via the secured connection between the carriage 413 and the retraction attachment mount 221. In such a circumstance, based at least in part on the magnitude of the pulling force received by the retraction attachment 220, the force characterization attachment carriage 413 may be configured to move along the force characterization attachment track 411 in the direction of the pulling force. For example, in such a circumstance, the second end 414B of the force characterization attachment carriage user interface mount 414 may comprise a hooked element configured to engage the force characterization attachment sensor interface 433 by applying the received pulling force thereto. As used in conjunction with the force characterization assembly 400, the retraction attachment 220 may be used in force characterization exercises to gauge the force that the jaw of a user is able to generate in a retraction direction.

Further, in various embodiments, the protraction attachment mount 230 (as shown in FIGS. 7 and 8A-8C) may be configured to be selectively attached to the force characterization attachment carriage 413 via a hooked connection, a nut-and-bolt connection, or any other fastening means configured to prevent the protraction attachment 230 from moving relative to the passive motion attachment carriage 413. In various embodiments, the protraction attachment interface 233 may be configured to receive a pushing force from the jaw of a user (e.g., from the chin of a user) at the outer surface 233A, wherein the protraction attachment 230 has been positioned below the mouth and substantially adjacent the front chin of a user. For example, wherein the protraction element 230 is attached to the force characterization attachment carriage user interface mount 414 illustrated in FIG. 11, a user may protract the jaw so as to generate a pushing force in the positive x-direction (e.g., the direction towards the force characterization attachment sensor assembly 430). The protraction attachment 230 may be configured to transmit the force received at the protraction attachment interface 233 to the force characterization attachment carriage 413 via the secured connection between the carriage 413 and the protraction attachment mount 231. In such a circumstance, based at least in part on the magnitude of the pushing force received by the protraction attachment 230, the force characterization attachment carriage 413 may be configured to move along the force characterization attachment track 411 in the direction of the pushing force. As used in conjunction with the force characterization attachment assembly 400, the protraction attachment 230 may be used in force characterization exercises to gauge the force that the jaw of a user is able to generate in a protraction direction.

Further, in various embodiments, the elevation attachment mount (as shown in FIGS. 7 and 8A-8C) may be configured to be selectively attached to the force characterization attachment carriage 413 via a pinned connection, a nut-and-bolt connection, or any other fastening means configured to prevent the elevation attachment 240 from moving relative to the force characterization attachment carriage 413. In various embodiments, the one or more elevation attachment interfaces 243 may be configured to receive a pushing force from the jaw of a user (e.g., from the top surface of the bottom set of teeth of a user) at the lower surface 243A, wherein the elevation attachment 240 has been arranged so as to be at least partially disposed inside the mouth of the user. For example, wherein the elevation element 240 is attached to the force characterization attachment carriage user interface mount 414 illustrated in FIG. 11 and wherein the apparatus is configured in an elevation exercise configuration, the user may elevate the jaw so as to generate a pushing force in at least generally the positive y-direction (e.g., in a generally upward direction). The elevation attachment 240 may be configured to transmit the force received at the one or more elevation attachment interfaces 243 to the force characterization attachment carriage 413 via the secured connection between the carriage 413 and the elevation attachment mount 241 at the first end 414A of the force characterization attachment carriage user interface mount 414. In such a circumstance, based at least in part on the magnitude of the pushing force received by the elevation attachment 240, the force characterization attachment carriage 413 may be configured to move along the progressive resistance attachment track 211 in the direction of the pushing force (e.g., toward the force characterization attachment sensor assembly 430). In various embodiments, as used in conjunction with the force characterization attachment assembly 400, the elevation attachment 240 may be used in force characterization exercises to gauge the force that the jaw of a user is able to generate in an elevation direction.

In various embodiments, a chin pad (as shown in FIGS. 7 and 8A-8C) may comprise an element attached to the force characterization attachment carriage 413 (e.g. the force characterization attachment carriage user interface mount 414). In various embodiments, the chin pad may be positioned at least substantially perpendicular to the central axis of the force characterization attachment track 411 with a surface area configured receive a pushing force from the jaw of a user (e.g., from the side of the chin of the user) upon the user moving the jaw in a lateral direction towards the chin pad 250, wherein chin pad 250 is positioned adjacent the side of the jaw of the user. For example, the user may move the jaw laterally into the chin pad 250 so as to generate a pushing force in the positive x-direction (e.g., the direction toward the force characterization attachment sensor assembly 430). The chin pad 250 may be configured to transmit the received force to the force characterization attachment carriage 413. In such a circumstance, based at least in part on the magnitude of the pushing force received by the chin pad 250, the force characterization attachment carriage 413 may be configured to move along the force characterization attachment track 411 in the direction of the pushing force. In various embodiments, the force characterization attachment assembly 400 may be rotated about the vertical axis of the vertical frame attachment arm 180 degrees, as described herein, such that that chin pad 250 may be configured to engage either side of the jaw of a user. In various embodiments, as used in conjunction with the force characterization attachment assembly 400, the chin pad 250 may be used in force characterization exercises to gauge the force that the jaw of a user is able to generate in either lateral direction.

In various embodiments, the force characterization attachment assembly 400 may comprise a force characterization attachment sensor assembly 430. The force characterization attachment sensor assembly 430 may be configured to interact with the force characterization attachment carriage 413 (e.g., the second end 414B of the force characterization attachment carriage user interface mount 414) so as to receive a force transmitted therefrom, the force being at least substantially similar to the force transmitted from the jaw of a user to the force characterization attachment carriage 413 (e.g., the first end 414A of the force characterization attachment carriage user interface mount 414). In various embodiments, the force characterization attachment sensor assembly 430 may comprise a force characterization attachment sensor frame 431, a force characterization attachment sensor element 432, and a force characterization attachment sensor interface 433. In various embodiments, the force characterization attachment sensor frame 431 may comprise one or more components secured to the force characterization attachment body 410 and configured to secure the force characterization attachment sensor element 432 in a desired position. As described herein, the force characterization attachment sensor frame 431 may stabilize the force characterization attachment sensor element 432 in a desired position such that the second end 414B of the force characterization attachment carriage user interface mount 414 can engage the force characterization attachment sensor interface 433. For example, in various embodiments, the force characterization attachment sensor frame 431 may secure the force characterization attachment sensor element 432 in a substantially horizontal position wherein the central axis of the force characterization attachment sensor element 432 is at least substantially coaxial with the travel path of the second end 414B of the force characterization attachment carriage user interface mount 414.

In various embodiments, the force characterization attachment sensor element 432 may comprise a measurement device configured to measure the force applied thereto by the force characterization attachment carriage 413 (e.g., the second end 414B of the force characterization attachment carriage user interface mount 414). In various embodiments, the force characterization attachment sensor element 432 may comprise a force characterization attachment sensor interface 433 configured to receive one or more forces being transmitted to the force characterization attachment sensor element 432. For example, the force characterization attachment sensor element 432 may be configured to determine the magnitude of either a pulling force or a pushing force applied to the force characterization attachment sensor interface 433 in a positive or negative direction along the central axis of the force characterization attachment sensor element 432. As a non-limiting example, the force characterization attachment sensor element 432 may be a load cell or any other commercially available measurement device that would be operable within an exemplary apparatus described herein, such as, for example, a Loadstar™ Sensors RSB2 Steel Button Load Cell. The force characterization attachment sensor element 432 may be a digital sensor device configured to electronically communicate a measured force to one or more remote output devices and/or computers.

As described herein, the force characterization attachment sensor interface 433 may comprise a substantially flat outer surface positioned facing toward the second end 414B of the force characterization attachment carriage user interface mount 414. Alternatively, in various embodiments, the force characterization attachment sensor interface 433 may comprise a hooked element, a plunger element, and/or the like such that the force characterization attachment sensor interface 433 may be configured to receive a pulling force applied thereto via the force characterization attachment carriage 413.

e. Hyoid Motion Attachment Assembly

Figure 12:
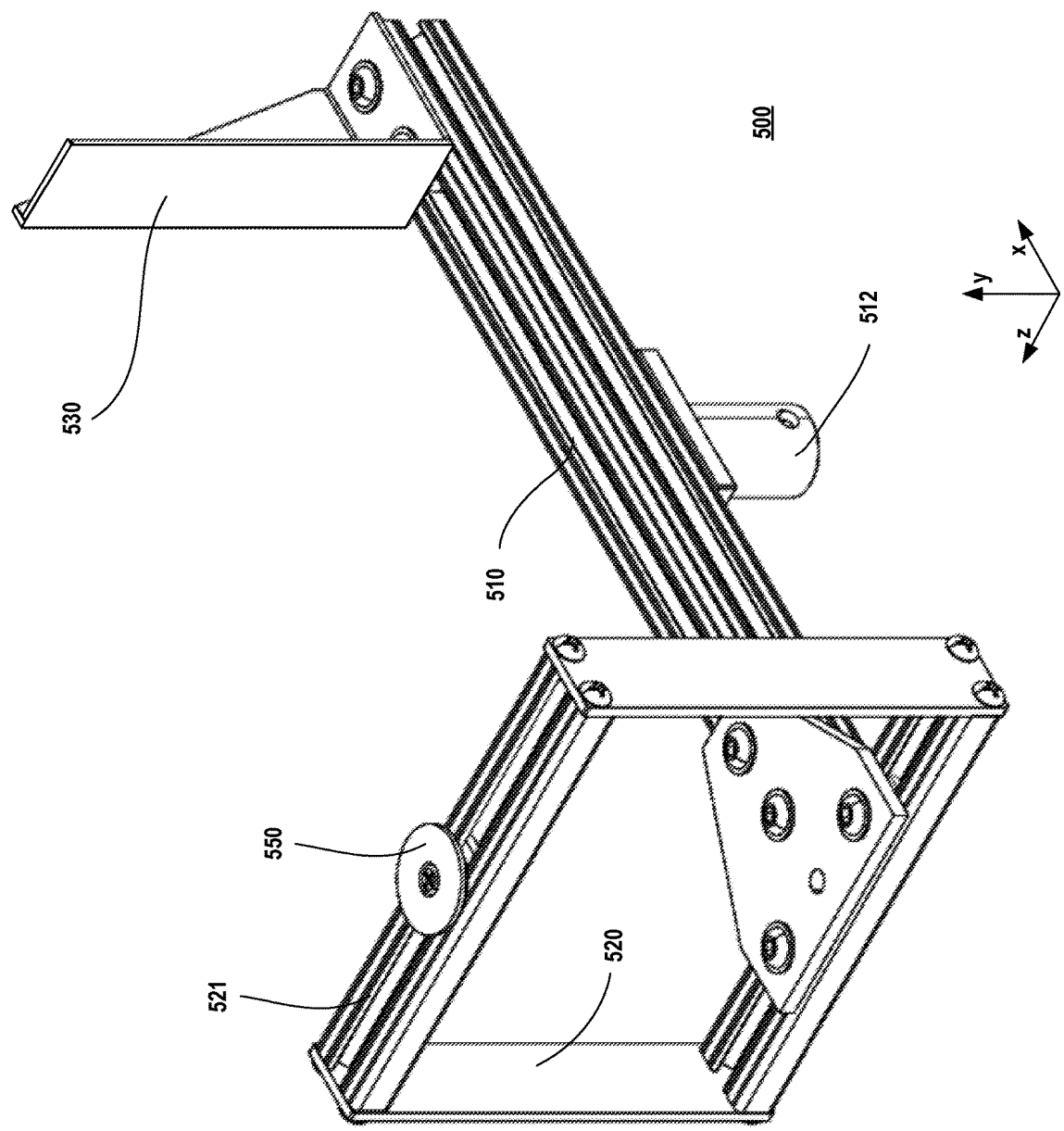
FIG. 12 illustrates a perspective view of an exemplary apparatus according to an embodiment as described herein.

FIG. 12 illustrates an exemplary apparatus according to an embodiment as described herein. In particular, FIG. 12 illustrates an exemplary hyoid motion attachment assembly 500. In various embodiments, a hyoid motion attachment assembly 500 may comprise a hyoid motion frame attachment interface 512, a hyoid motion attachment body 510, a hyoid motion attachment window 520, and a hyoid motion attachment indicator display surface 530. As described herein, a hyoid motion attachment assembly 500 may be configured to facilitate the evaluation of jaw-related muscles, such as, for example, the Suprahyoid Muscle and/or Infrahyoid Muscle of a user, by encouraging user activation thereof and measuring the range of motion of the muscles.

In various embodiments, a hyoid motion attachment assembly 500 may comprise a hyoid motion frame attachment interface 512 configured to engage an interchangeable functional assembly interface 112 of an exemplary frame assembly 100 so as to operably secure the hyoid motion frame attachment interface 512 to the frame assembly 100. As described above, although illustrated in FIG. 12 as engaging the interchangeable functional assembly interface 112 via a pinned connection, it should be understood that the hyoid motion frame attachment interface 512 may comprise any mechanism and/or fastening means configured to interact with the interchangeable functional assembly interface 112 so as to prevent the hyoid motion attachment assembly 500 from moving relative to the interchangeable functional assembly interface 112.

In various embodiments, the hyoid motion attachment assembly 500 comprise may comprise a hyoid motion attachment body 510 that is fixedly attached to the hyoid motion frame attachment interface 512. The hyoid motion attachment body 510 may function as a foundational element configured to either directly or indirectly support each of the other components of the hyoid motion attachment assembly 500. In various embodiments, the hyoid motion attachment body 510 may comprise an elongated rigid member extending along a central axis that is perpendicular to the axis along which the hyoid motion frame attachment interface 512 may extend. The hyoid motion attachment body 510 may comprise at least one at least substantially flat surface. In various embodiments, a hyoid motion attachment indicator display surface 530 may be secured on a substantially flat top surface of the hyoid motion attachment body 510 and centered about the central axis of the hyoid motion attachment body 510.

As described herein, the hyoid motion attachment assembly 500 comprise may comprise a hyoid motion attachment window 520 disposed about a first end of the hyoid motion attachment body 510. The hyoid motion attachment window 520 may be fixedly attached to the hyoid motion attachment body 510, extending in an upward direction perpendicular to the central axis of the hyoid motion attachment body 510. In various embodiments, a hyoid motion attachment window 520 may comprise a hollow outer frame element comprising an upper surface 521 configured such that a jaw (e.g., the bottom of a chin of a user) may be placed thereon. In various embodiments the hyoid motion attachment window 520 may comprise a chin pad 550 secured on top of the upper surface 521 and configured to interface with the jaw of the user. For example, the hyoid motion attachment window 520 may be configured such that when a jaw of a user is placed upon the upper surface 521 of the hyoid motion attachment window 520, at least a portion of a front neck region of the user corresponding to the hyoid bone may be positioned below the upper surface 521 and facing in a direction that is at least substantially parallel to the central axis of the hyoid motion attachment body 510 and at least substantially perpendicular to a hyoid motion attachment indicator display surface 530 disposed about the second end of the hyoid motion attachment body 510.

In various embodiments, a hyoid motion attachment indicator display surface 530 may comprise a substantially flat surface that may be fixedly attached to the hyoid motion attachment body 510, extending in an upward direction perpendicular to the central axis of the hyoid motion attachment body 510. In various embodiments, a hyoid motion attachment indicator display surface 530 may be configured to display an image of a target and/or other locale reference points such that a hyoid motion indicator device, such as, for example, a laser, operably attached to the at least a portion of a front neck region of the user may display on the hyoid motion attachment indicator display surface 530

As described herein, the hyoid motion attachment assembly 500 may further comprise a hyoid motion indicator device (not picture). In various embodiments, a hyoid motion indicator device may comprise a mobile device that may be attached to at least a portion of a front neck region of a user. The hyoid motion indicator may be configured to project a hyoid motion indicator, such as, for example, a laser, a beam of light, and/or the like, in a linear direction extending away from the at least a portion of the front neck region of the user. As described, the hyoid motion indicator device may be configured on the at least a portion of the front neck region of the user such that the hyoid motion indicator may be projected onto the hyoid motion attachment indicator display surface 530 in a resting configuration. In various embodiments, the hyoid motion indicator may be projected onto the hyoid motion attachment indicator display surface 530 in a first position when the user is in a resting configuration and a second position when the aforementioned muscles corresponding to the activation of the hyoid bone are stimulated (i.e. moved). For example, the movement of the at least a portion of the front neck region of the user and the resulting displacement of the hyoid motion indicator on the hyoid motion attachment indicator display surface 530 may facilitate the evaluation of the above referenced jaw-related muscles by encouraging user activation thereof and measuring the range of motion of the muscles.

II. EXEMPLARY METHODS OF USE

In various embodiments of the present invention, methods are provided for evaluating jaw movement characteristics of a user. Notably, there is need in the dental and medical fields to collect data regarding the range of motion of the temporomandibular joint (TMJ) and the forces produced by the muscles of the TMJ. This data is useful for TMJ research, in education, and in clinical settings to assist in formulating treatment plans for disorders and damage to the TMJ and its surrounding soft tissue. It is also useful in Dentistry to better understand and treat occlusal relationships. There is further utility in measuring range of motion of, and forces produced by the TMJ and its surrounding musculature for the purpose of pre-orthodontic TMJ alignment in regard to the musculature. Further, a comprehensive measuring tool would enhance the ability to design exercise protocols to enhance the previously mentioned applications as well as in the design of protocols to strengthen the musculature of the TMJ to prevent injuries that can occur in a variety of contact sports.

Still further, diminished range of motion of the temporomandibular joint (TMJ) can occur for a variety of reasons, the most extreme of these is in cases where a jaw must be wired closed for postoperative recovery. Injury, pathology and general dysfunction can also lead to decreased range of motion of the TMJ. In order to restore full range of motion, exercise protocols, beginning with passive range of motion exercise, are often indicated. As progress occurs, active assisted range of motion exercises are indicated until a joint can be moved independently (active exercise) throughout its full range of motion. Notably, range of motion exercises through all three planes of movement are more effective than those exercises that address mandibular depression in isolation.

The following paragraphs generally describe exemplary methods of exercising and/or quantifying jaw strength in six distinct jaw movement directions.

a. Active Range of Motion Jaw Evaluation

In various embodiments, an exemplary method may be provided for evaluating the jaw movement characteristics of the jaw of a user through an active range of motion jaw exercise. In one exemplary method according to various embodiments, a jaw exercise system, as described herein, may be provided. In various embodiments, as described herein, a user may secure a frame assembly of the jaw exercise system to an effectively immobilized surface or member in an at least substantially stationary position via a stabilizing interface assembly. A user may be positioned so as to face the stabilized frame assembly in a position centered about the central axis of the horizontal frame arm. As described above with respect to FIG. 7, the user may be facing in the positive x-direction with the secured frame assembly positioned directly in front of the user.

In various embodiments, a progressive resistance attachment assembly may be securely fastened to an interchangeable functional attachment interface of the frame assembly, as described above. In various embodiments, exemplary methods may be provided for evaluating the jaw movement characteristics through one or more active range of motion jaw exercises in each of six jaw motion directions.

i. Retraction

In various embodiments, the progressive resistance attachment assembly secured to the interchangeable functional attachment interface of the frame assembly may be positioned such that the central axis of the progressive resistance attachment body is at least substantially coplanar about a vertical plane with and at least substantially parallel to a central axis of the horizontal frame arm of the frame assembly. Further, the progressive resistance attachment assembly may be positioned such that the primary pulley wheel secured thereto via a primary pulley arm is facing away from the user.

As described herein and as illustrated in FIGS. 7 and 8A-8C, a retraction attachment may be selectively attached to the progressive resistance attachment carriage such that a retraction attachment interface thereof extends in a direction toward the user. In various embodiments, said exemplary user may adjust the height of, for example, the vertical frame attachment arm such that the retraction attachment interface disposed on the progressive resistance attachment assembly is aligned and leveled with the mouth of the user. Once the jaw exercise system is properly configured in the retraction configuration described above and aligned with the user, the user may engage the retraction attachment interface. For example, the user may arrange the retraction attachment so as to be at least partially disposed inside the mouth of the user, wherein the retraction attachment interface is engaged with the inside of the bottom teeth of a user. Upon engaging the retraction attachment interface, the user may selectively add a resistance force to be transmitted to the jaw of the user via the retraction attachment interface. For example, as described herein, the resistance force may be generated by one or more weights selectively disposed at an opposite end of a resistance rope attached to the progressive resistance attachment carriage. The user may add an amount of weight corresponding to a desired jaw retraction strength. The user may then extend the jaw forward (e.g., in the positive x-direction) so as to lower the suspended weight associated with the resistance force, and subsequently may retract the jaw backward in the negative x-direction (e.g., the direction away from the pulley) so as to generate a pulling force. As described herein, in various embodiments, the pulling force generated by the user during the retraction of the jaw is sufficiently larger than the resistance force generated by the weights. In various embodiments, the aforementioned extension and retraction of the jaw engaged with the retraction attachment interface while subjected to the resistance force may be repeated according to user preference.

ii. Protraction

In various embodiments, the progressive resistance attachment assembly secured to the interchangeable functional attachment interface of the frame assembly may be positioned such that the central axis of the progressive resistance attachment body is at least substantially coplanar about a vertical plane with and at least substantially parallel to a central axis of the horizontal frame arm of the frame assembly. Further, the progressive resistance attachment assembly may be positioned such that the primary pulley wheel secured thereto via a primary pulley arm is facing toward the user. For example, a user may rotate the progressive resistance attachment assembly 180 degrees about the central axis of the vertical frame attachment assembly in order to transition from the above-described retraction configuration to a protraction configuration.

As described herein and as illustrated in FIGS. 7 and 8A-8C, a protraction attachment may be selectively attached to the progressive resistance attachment carriage such that a protraction attachment interface thereof extends in a direction toward the user. In various embodiments, said exemplary user may adjust the height of, for example, the vertical frame attachment arm such that the protraction attachment interface disposed on the progressive resistance attachment assembly is aligned and leveled with the front of the chin of the user. Once the jaw exercise system is properly configured in the protraction configuration described above and aligned with the user, the user may engage the protraction attachment interface. For example, the user may arrange the protraction attachment so as to be physically engaged with the front of the chin of the user. Upon engaging the protraction attachment interface, the user may selectively add a resistance force to be transmitted to the jaw of the user via the protraction attachment interface. For example, as described herein, the resistance force may be generated by one or more weights selectively disposed at an opposite end of a resistance rope attached to the progressive resistance attachment carriage. The user may add an amount of weight corresponding to a desired jaw protraction strength. The user may then extend the jaw backward (e.g., in the negative x-direction, as described above relative to the positioning of the user) so as to lower the suspended weight associated with the resistance force, and subsequently may extend the jaw forward in the positive x-direction (e.g., the direction toward the pulley) so as to generate a pushing force at the protraction attachment interface. As described herein, in various embodiments, the pushing force generated by the user during the protraction of the jaw is sufficiently larger than the resistance force generated by the weights. In various embodiments, the aforementioned extension and retraction of the jaw engaged with the protraction attachment interface subjected to a resistance force may be repeated according to user preference.

iii. Left Lateral Deviation

In various embodiments, the progressive resistance attachment assembly secured to the interchangeable functional attachment interface of the frame assembly may be positioned such that the central axis of the progressive resistance attachment body is at least substantially perpendicular to a central axis of the horizontal frame arm of the frame assembly. Further, the progressive resistance attachment assembly may be positioned such that the primary pulley wheel secured thereto via a primary pulley arm is on a rightward portion of the progressive resistance attachment body relative to the user. For example, a user may rotate the progressive resistance attachment assembly 90 degrees counter-clockwise about the central axis of the vertical frame attachment assembly in order to transition from the above-described protraction configuration to a left lateral deviation configuration.

As described herein, a chin pad may be selectively attached to the progressive resistance attachment carriage and positioned such that the face of the chin pad may be at least substantially perpendicular to the central axis of the progressive resistance attachment body. In various embodiments, the exemplary user may adjust the height of, for example, the vertical frame attachment arm such that the chin pad disposed on the progressive resistance attachment assembly is aligned and leveled with the left side of the chin of the user. Once the jaw exercise system is properly configured in the left lateral deviation configuration described above and aligned with the user, the user may engage the chin pad. For example, the user may arrange the chin pad so as to be physically engaged with the left side of the chin of the user. Upon engaging the chin pad, the user may selectively add a resistance force to be transmitted to the jaw of the user via the chin pad. For example, as described herein, the resistance force may be generated by one or more weights selectively disposed at an opposite end of a resistance rope attached to the progressive resistance attachment carriage. The user may add an amount of weight corresponding to a desired jaw left lateral deviation strength. The user may then extend the jaw in a rightward lateral direction (e.g., in the positive z-direction, as described above relative to the positioning of the user) so as to lower the suspended weight associated with the resistance force, and subsequently may extend the jaw in a leftward lateral direction (e.g., in the negative z-direction) so as to generate a pushing force at the chin pad. As described herein, in various embodiments, the pushing force generated by the user during the left lateral deviation of the jaw is sufficiently larger than the resistance force generated by the weights. In various embodiments, the aforementioned rightward and leftward lateral movements of the of the jaw engaged with the chin pad subjected to a resistance force may be repeated according to user preference.

iv. Right Lateral Deviation

In various embodiments, the progressive resistance attachment assembly secured to the interchangeable functional attachment interface of the frame assembly may be positioned such that the central axis of the progressive resistance attachment body is at least substantially perpendicular to a central axis of the horizontal frame arm of the frame assembly. Further, the progressive resistance attachment assembly may be positioned such that the primary pulley wheel secured thereto via a primary pulley arm is on a leftward portion of the progressive resistance attachment body relative to the user. For example, a user may rotate the progressive resistance attachment assembly 180 degrees about the central axis of the vertical frame attachment assembly in order to transition from the above-described a left lateral deviation configuration to a right lateral deviation configuration.

As described herein, a chin pad may be selectively attached to the progressive resistance attachment carriage and positioned such that the face of the chin pad may be at least substantially perpendicular to the central axis of the progressive resistance attachment body. In various embodiments, the exemplary user may adjust the height of, for example, the vertical frame attachment arm such that the chin pad disposed on the progressive resistance attachment assembly is aligned and leveled with the left side of the chin of the user. Once the jaw exercise system is properly configured in the right lateral deviation configuration described above and aligned with the user, the user may engage the chin pad. For example, the user may arrange the chin pad so as to be physically engaged with the right side of the chin of the user. Upon engaging the chin pad, the user may selectively add a resistance force to be transmitted to the jaw of the user via the chin pad. For example, as described herein, the resistance force may be generated by one or more weights selectively disposed at an opposite end of a resistance rope attached to the progressive resistance attachment carriage. The user may add an amount of weight corresponding to a desired jaw right lateral deviation strength. The user may then extend the jaw in a leftward lateral direction (e.g., in the negative z-direction, as described above relative to the positioning of the user) so as to lower the suspended weight associated with the resistance force, and subsequently may extend the jaw in a rightward lateral direction (e.g., in the positive z-direction) so as to generate a pushing force at the chin pad. As described herein, in various embodiments, the pushing force generated by the user during the right lateral deviation of the jaw is sufficiently larger than the resistance force generated by the weights. In various embodiments, the aforementioned leftward and rightward lateral movements of the of the jaw engaged with the chin pad subjected to a resistance force may be repeated according to user preference.

v. Elevation

In various embodiments, the progressive resistance attachment assembly secured to the interchangeable functional attachment interface of the frame assembly may be positioned such that the central axis of the progressive resistance attachment body is at least substantially coplanar about a vertical plane with and at least substantially parallel to a central axis of the horizontal frame arm of the frame assembly. The progressive resistance attachment assembly may be positioned such that the primary pulley wheel secured thereto via a primary pulley arm is facing toward the user. For example, a user may rotate the progressive resistance attachment assembly 90 degrees counter-clockwise about the central axis of the vertical frame attachment assembly in order to transition from the above-described right lateral deviation configuration to an intermediate configuration that may enable a user to further configure the progressive resistance assembly attachment in an elevation configuration. As described herein, the progressive resistance attachment assembly may be angularly adjusted relative to the horizontal plane such that an end of the progressive resistance attachment assembly nearest the user (e.g., the end of the progressive resistance attachment assembly comprising the primary pulley wheel) moves in a downward direction and the progressive resistance attachment body extends in both the positive x-direction and the positive y-direction (e.g., relative to the position of the user, as described herein). The progressive resistance attachment body may extend upward and away from the user in the positive x-direction such that the progressive resistance attachment body is arranged at between a 45 and 90 degree angle (e.g., a 70 degree angle) relative to the horizontal plane along which it extends when configured in, for example, the protraction configuration, as described herein. In various embodiments, the angular configuration of the progressive resistance attachment assembly may be such that it accommodates a natural angular motion of the jaw. For example, in various embodiments, the angular configuration of the multi-axis attachment interface hinge may be selectively adjusted such that the progressive resistance attachment assembly secured thereto may be similarly adjusted to a desired angular position. In various embodiments, a user may disengage a secondary pulley arm pivot joint such that the secondary pulley arm may be removed from a locked configuration and freed to rotatably move about the secondary pulley arm pivot joint relative to the progressive resistance attachment body as the bodily is angularly adjusted.

As described herein, an elevation attachment may be selectively attached to the progressive resistance attachment carriage such that an elevation attachment interface thereof extends in a direction toward the user. In various embodiments, said exemplary user may adjust the height of, for example, the vertical frame attachment arm such that the elevation attachment interface disposed on the progressive resistance attachment assembly is aligned and leveled with the mouth of the user. In various embodiments, the elevation attachment may comprise either a single elevation attachment interface or two elevation attachment interfaces, which may correspond to a user exercising only one lateral side of the jaw or both lateral sides of the jaw at a time, respectively.

Once the jaw exercise system is properly configured in the elevation configuration described above and aligned with the user, the user may engage the elevation attachment interface. For example, the user may arrange the elevation attachment so as to be at least partially disposed inside the mouth of the user, wherein the elevation attachment interface is engaged with the top surface of the bottom teeth of a user. Upon engaging the elevation attachment interface, the user may selectively add a resistance force to be transmitted to the jaw of the user via the elevation attachment interface. For example, as described herein, the resistance force may be generated by one or more weights selectively disposed at an opposite end of a resistance rope attached to the progressive resistance attachment carriage. The user may add an amount of weight corresponding to a desired jaw elevation strength. The user may then open the jaw in a substantially downward direction (e.g., in a direction at least substantially parallel with the angled center axis of the progressive resistance attachment assembly) so as to lower the suspended weight associated with the resistance force, and subsequently may elevate the jaw in a substantially upward direction so as to apply a pushing force to the one or more elevation attachment interfaces. As described herein, in various embodiments, the pushing force generated by the user during the elevation of the jaw is sufficiently larger than the resistance force generated by the weights. In various embodiments, the aforementioned opening and elevation of the jaw engaged with the one or more elevation attachment interfaces while subjected to the resistance force may be repeated according to user preference.

vi. Depression

In various embodiments, the progressive resistance attachment assembly secured to the interchangeable functional attachment interface of the frame assembly may be positioned such that the central axis of the progressive resistance attachment body is at least substantially coplanar about a vertical plane with and at least substantially parallel to a central axis of the horizontal frame arm of the frame assembly. The progressive resistance attachment assembly may be positioned such that the primary pulley wheel secured thereto via a primary pulley arm is facing away from the user. For example, a user may rotate the progressive resistance attachment assembly 180 degrees about the central axis of the vertical frame attachment assembly in order to transition from the above-described elevation configuration to an intermediate configuration that may enable a user to further configure the progressive resistance assembly attachment in a depression configuration. As described herein, the progressive resistance attachment assembly may be angularly adjusted relative to the horizontal plane such that an end of the progressive resistance attachment assembly nearest the user (e.g., the end of the progressive resistance attachment assembly opposite the primary pulley wheel) moves in a downward direction and the progressive resistance attachment body extends in both the positive x-direction and the positive y-direction (e.g., relative to the position of the user, as described herein). The progressive resistance attachment body may extend upward and away from the user in the positive x-direction such that the progressive resistance attachment body is arranged at between a 45 and 90 degree angle (e.g., an 80 degree angle) relative to the horizontal plane along which it extends when configured in, for example, the protraction configuration, as described herein. In various embodiments, the angular configuration of the progressive resistance attachment assembly may be such that it accommodates a natural angular motion of the jaw. For example, in various embodiments, the angular configuration of the multi-axis attachment interface hinge may be selectively adjusted such that the progressive resistance attachment assembly secured thereto may be similarly adjusted to a desired angular position. In various embodiment, when the progressive resistance attachment assembly is angularly configured in a depression configuration, as described above, the resistance rope may engage both the primary pulley wheel and the secondary pulley wheel such that the weights attached to the end of the resistance rope travel along a substantially vertical axis that is extended away from the progressive resistance attachment body. In various embodiments, a user may selectively adjust the length of the resistance rope so as to ensure that the suspended configuration of the weights is maintained throughout the corresponding range of motion.

As described herein, a chin pad may be selectively attached to the progressive resistance attachment carriage and positioned such that the face of the chin pad may be at least substantially perpendicular to the central axis of the progressive resistance attachment body. In various embodiments, the exemplary user may adjust the height of, for example, the vertical frame attachment arm such that the chin pad disposed on the progressive resistance attachment assembly is aligned and leveled with the bottom of the chin of the user. Once the jaw exercise system is properly configured in the depression configuration described above and aligned with the user, the user may engage the chin pad. For example, the user may arrange the chin pad so as to be physically engaged with the bottom of the chin of the user. Upon engaging the chin pad, the user may selectively add a resistance force to be transmitted to the jaw of the user via the chin pad. For example, as described herein, the resistance force may be generated by one or more weights selectively disposed at an opposite end of a resistance rope attached to the progressive resistance attachment carriage. The user may then elevate the jaw in a substantially upward direction (e.g., in a direction at least substantially parallel with the angled center axis of the progressive resistance attachment assembly) so as to lower the suspended weight associated with the resistance force, and subsequently may open the jaw in the at least substantially downward direction so as to generate a pushing force applied to the chin pad. As described herein, in various embodiments, the pushing force generated by the user during the elevation of the jaw is sufficiently larger than the resistance force generated by the weights. In various embodiments, the aforementioned opening and elevation of the jaw engaged with the one or more elevation attachment interfaces while subjected to the resistance force may be repeated according to user preference.

b. Passive Range of Motion Jaw Evaluation

In various embodiments, an exemplary method may be provided for evaluating the jaw movement characteristics of the jaw of a user through an active range of motion jaw exercise. In one exemplary method according to various embodiments, a jaw exercise system, as described herein, may be provided. In various embodiments, as described herein, a user may secure a frame assembly of the jaw exercise system to an effectively immobilized surface or member in an at least substantially stationary position via a stabilizing interface assembly. A user may be positioned so as to face the stabilized frame assembly in a position centered about the central axis of the horizontal frame arm. As described herein, the user may be facing in the positive x-direction with the secured frame assembly positioned directly in front of the user.

In various embodiments, a passive motion attachment assembly, such as, for example, the exemplary embodiment illustrated in FIG. 9, may be securely fastened to an interchangeable functional attachment interface of the frame assembly, as described herein. In various embodiments, exemplary methods may be provided for evaluating the jaw movement characteristics through one or more passive range of motion jaw exercises in each of six jaw motion directions.

i. Retraction

In various embodiments, the passive motion attachment assembly secured to the interchangeable functional attachment interface of the frame assembly may be positioned such that the central axis of the passive motion attachment body is at least substantially coplanar about a vertical plane with and at least substantially parallel to a central axis of the horizontal frame arm of the frame assembly. Further, the passive motion attachment assembly may be positioned such that the component of the passive motion attachment carriage configured to securely attach one or more user interface attachments thereto (e.g., a passive motion attachment carriage user interface mount) is facing toward the user.

As described herein, a protraction attachment may be selectively attached to the passive motion attachment carriage such that a protraction attachment interface thereof extends in a direction toward the user. In various embodiments, the exemplary user may adjust the height of, for example, the vertical frame attachment arm such that the protraction attachment interface disposed on the passive motion attachment assembly is aligned and leveled with the front of the chin of the user. Once the jaw exercise system is properly configured in the protraction configuration described above and aligned with the user, the user may engage the protraction attachment interface. For example, the user may arrange the protraction attachment so as to be physically engaged with the front of the chin of the user so as to establish a substantially flush interface between the chin and the chin pad without transmitting any force therebetween.

Upon engaging the protraction attachment interface, the user may interact with a passive engagement force assembly so as to selectively generate an engagement force to be transmitted to the jaw of the user via the protraction attachment interface. For example, as described herein, the engagement force may be generated by user interaction with one or more user control interfaces, wherein the user interaction with, for example, one or more knobs, may result in a linear driving force being transmitted to the passive motion attachment carriage (e.g., in a negative x-direction). In various embodiments, the engagement force generated by said user interaction causes the passive motion attachment carriage, as well as the protraction attachment secured thereto, to move along the passive motion attachment track in a direction corresponding to the direction of the linear driving force. The magnitude of the force generated by the user to be transmitted to the protraction attachment engaged with the jaw of the user may be selectively determined based on a desired jaw range of motion in a retraction direction. For example, a user may selectively cause the passive motion attachment carriage to move along the passive motion attachment track, as described herein, in an engagement direction such that a pushing force is applied in the negative x-direction (e.g., the direction towards the user) at the jaw of the user. In such a circumstance, based at least in part on the magnitude of the pushing force applied to the jaw of the user, the jaw may move in the direction of the pushing force in a retraction direction (e.g., extending toward the spine of the user). In various embodiments, the aforementioned application of the engagement force to the jaw engaged with the protraction attachment interface may be repeated according to user preference.

ii. Protraction

In various embodiments, the passive motion attachment assembly secured to the interchangeable functional attachment interface of the frame assembly may be positioned such that the central axis of the passive motion attachment body is at least substantially coplanar about a vertical plane with and at least substantially parallel to a central axis of the horizontal frame arm of the frame assembly. Further, the passive motion attachment assembly may be positioned such that the component of the passive motion attachment carriage configured to securely attach one or more user interface attachments thereto (e.g., a passive motion attachment carriage user interface mount) is facing toward the user.

As described herein, a retraction attachment may be selectively attached to the passive motion attachment carriage such that a retraction attachment interface thereof extends in a direction toward the user. In various embodiments, the exemplary user may adjust the height of, for example, the vertical frame attachment arm such that the retraction attachment interface disposed on the passive motion attachment assembly is aligned and leveled with the mouth of the user. Once the jaw exercise system is properly configured in the retraction configuration described above and aligned with the user, the user may engage the retraction attachment interface. For example, the user may arrange the retraction attachment so as to be at least partially disposed inside the mouth of the user, wherein the retraction attachment interface is engaged with the inside of the bottom teeth of a user without applying any force thereto.

Upon engaging the retraction attachment interface, the user may interact with a passive engagement force assembly so as to selectively generate an engagement force to be transmitted to the jaw of the user via the retraction attachment interface. For example, as described herein, the engagement force may be generated by user interaction with one or more user control interfaces, wherein the user interaction with, for example, one or more knobs, may result in a linear driving force being transmitted to the passive motion attachment carriage (e.g., in a negative x-direction). In various embodiments, the engagement force generated by said user interaction causes the passive motion attachment carriage, as well as the retraction attachment secured thereto, to move along the passive motion attachment track in a direction corresponding to the direction of the linear driving force. The magnitude of the force generated by the user to be transmitted to the retraction attachment engaged with the jaw of the user may be selectively determined based on a desired jaw range of motion in a protraction direction. For example, a user may selectively cause the passive motion attachment carriage to move along the passive motion attachment track, as described herein, in an engagement direction such that a pulling force is applied in the positive x-direction (e.g., the direction away from the user) at the jaw of the user. In such a circumstance, based at least in part on the magnitude of the pulling force applied to the jaw of the user, the jaw may move in the direction of the pulling force in a protraction direction (e.g., extending away from the user). In various embodiments, the aforementioned application of the engagement force to the jaw engaged with the retraction attachment interface may be repeated according to user preference.

iii. Left Lateral Deviation

In various embodiments, the passive motion attachment assembly secured to the interchangeable functional attachment interface of the frame assembly may be positioned such that the central axis of the passive motion attachment body is at least substantially perpendicular to a central axis of the horizontal frame arm of the frame assembly. For example, a user may rotate the passive motion attachment assembly 90 degrees about the central axis of the vertical frame attachment assembly in order to transition from the above-described protraction configuration to a left lateral deviation configuration.

As described herein, a chin pad may be selectively attached to the passive motion attachment carriage and positioned such that the face of the chin pad may be at least substantially perpendicular to the central axis of the passive motion attachment body. In various embodiments, the exemplary user may adjust the height of, for example, the vertical frame attachment arm such that the chin pad disposed on the passive motion attachment assembly is aligned and leveled with the right side of the chin of the user. Once the jaw exercise system is properly configured in the left lateral deviation configuration described above and aligned with the user, the user may engage the chin pad. For example, the user may arrange the chin pad so as to be physically engaged with the right side of the chin of the user so as to establish a substantially flush interface between the chin and the chin pad without transmitting any force therebetween.

Upon engaging the chin pad, the user may interact with a passive engagement force assembly so as to selectively generate an engagement force to be transmitted to the jaw of the user via the chin pad. For example, as described herein, the engagement force may be generated by user interaction with one or more user control interfaces, wherein the user interaction with, for example, one or more knobs, may result in a linear driving force being transmitted to the passive motion attachment carriage (e.g., in a leftward lateral direction relative to the user). In various embodiments, the engagement force generated by said user interaction causes the passive motion attachment carriage, as well as the chin pad secured thereto, to move along the passive motion attachment track in a direction corresponding to the direction of the linear driving force. The magnitude of the force generated by the user to be transmitted to the chin pad engaged with the jaw of the user may be selectively determined based on a desired jaw range of motion in a left lateral deviation direction. For example, a user may selectively cause the passive motion attachment carriage to move along the passive motion attachment track, as described herein, in an engagement direction such that a pushing force is applied in the leftward lateral direction at the jaw of the user. In such a circumstance, based at least in part on the magnitude of the pushing force applied to the jaw of the user, the jaw may move in the direction of the pushing force in a left lateral deviation direction. In various embodiments, the aforementioned application of the engagement force to the jaw engaged with the chin pad may be repeated according to user preference.

iv. Right Lateral Deviation

In various embodiments, the passive motion attachment assembly secured to the interchangeable functional attachment interface of the frame assembly may be positioned such that the central axis of the passive motion attachment body is at least substantially perpendicular to a central axis of the horizontal frame arm of the frame assembly. For example, in various embodiments, a user may rotate the passive motion attachment assembly 180 degrees about the central axis of the vertical frame attachment assembly in order to transition from the above-described left lateral deviation configuration to a right lateral deviation configuration. Alternatively, in an exemplary embodiment wherein the passive motion attachment assembly comprises two chin pads arranged to face opposite directions (e.g., a rightward lateral direction and a leftward lateral direction), a user may simply rearrange the jaw such that a chin pad facing the user is disposed to the left of the user.

As described herein, a chin pad may be selectively attached to the passive motion attachment carriage and positioned such that the face of the chin pad may be at least substantially perpendicular to the central axis of the passive motion attachment body. In various embodiments, the exemplary user may adjust the height of, for example, the vertical frame attachment arm such that the chin pad disposed on the passive motion attachment assembly is aligned and leveled with the left side of the chin of the user. Once the jaw exercise system is properly configured in the right lateral deviation configuration described above and aligned with the user, the user may engage the chin pad. For example, the user may arrange the chin pad so as to be physically engaged with the left side of the chin of the user so as to establish a substantially flush interface between the chin and the chin pad without transmitting any force therebetween.

Upon engaging the chin pad, the user may interact with a passive engagement force assembly so as to selectively generate an engagement force to be transmitted to the jaw of the user via the chin pad. For example, as described herein, the engagement force may be generated by user interaction with one or more user control interfaces, wherein the user interaction with, for example, one or more knobs, may result in a linear driving force being transmitted to the passive motion attachment carriage (e.g., in a rightward lateral direction relative to the user). In various embodiments, the engagement force generated by said user interaction causes the passive motion attachment carriage, as well as the chin pad secured thereto, to move along the passive motion attachment track in a direction corresponding to the direction of the linear driving force. The magnitude of the force generated by the user to be transmitted to the chin pad engaged with the jaw of the user may be selectively determined based on a desired jaw range of motion in a right lateral deviation direction. For example, a user may selectively cause the passive motion attachment carriage to move along the passive motion attachment track, as described herein, in an engagement direction such that a pushing force is applied in the rightward lateral direction at the jaw of the user. In such a circumstance, based at least in part on the magnitude of the pushing force applied to the jaw of the user, the jaw may move in the direction of the pushing force in a right lateral deviation direction. In various embodiments, the aforementioned application of the engagement force to the jaw engaged with the chin pad may be repeated according to user preference.

v. Elevation

In various embodiments, the passive motion attachment assembly secured to the interchangeable functional attachment interface of the frame assembly may be positioned such that the central axis of the progressive resistance attachment body is at least substantially coplanar about a vertical plane with and at least substantially parallel to a central axis of the horizontal frame arm of the frame assembly. For example, a user may rotate the progressive resistance attachment assembly 90 degrees about the central axis of the vertical frame attachment assembly in order to transition from the above-described right lateral deviation configuration to an intermediate configuration that may enable a user to further configure the progressive resistance assembly attachment in an elevation configuration. As described herein, the passive motion attachment assembly may be angularly adjusted relative to the horizontal plane such that the end of the passive motion attachment assembly nearest the user moves in a downward direction and the passive motion attachment body extends in both the positive x-direction and the positive y-direction (e.g., relative to the position of the user, as described herein). The passive motion attachment body may extend upward and away from the user in the positive x-direction such that the passive motion attachment body is arranged at between a 45 and 90 degree angle (e.g., a 70 degree angle) relative to the horizontal plane along which it extends when configured in, for example, the protraction configuration, as described herein. In various embodiments, the angular configuration of the passive motion attachment assembly may be such that it accommodates a natural angular motion of the jaw. For example, in various embodiments, the angular configuration of the multi-axis attachment interface hinge may be selectively adjusted such that the passive motion attachment assembly secured thereto may be similarly adjusted to a desired angular position.

As described herein, a chin pad may be selectively attached to the passive motion attachment carriage and positioned such that the face of the chin pad may be at least substantially perpendicular to the central axis of the passive motion attachment body. In various embodiments, the exemplary user may adjust the height of, for example, the vertical frame attachment arm such that the chin pad disposed on the passive motion attachment assembly is aligned and leveled with the bottom of the chin of the user. Once the jaw exercise system is properly configured in the depression configuration described above and aligned with the user, the user may engage the chin pad. For example, the user may arrange the chin pad so as to establish a substantially flush interface between the bottom of the chin and the chin pad without transmitting any force therebetween.

Upon engaging the chin pad, the user may interact with a passive engagement force assembly so as to selectively generate an engagement force to be transmitted to the jaw of the user via the chin pad. For example, as described herein, the engagement force may be generated by user interaction with one or more user control interfaces, wherein the user interaction with, for example, one or more knobs, may result in a linear driving force being transmitted to the passive motion attachment carriage (e.g., in a substantially upward direction). In various embodiments, the engagement force generated by said user interaction causes the passive motion attachment carriage, as well as the chin pad secured thereto, to move along the passive motion attachment track in a direction corresponding to the direction of the linear driving force. The magnitude of the force generated by the user to be transmitted to the chin pad engaged with the jaw of the user may be selectively determined based on a desired jaw range of motion in an elevation direction. For example, a user may selectively cause the passive motion attachment carriage to move along the passive motion attachment track, as described herein, in an engagement direction such that a pushing force is applied in the upward direction at the jaw of the user. In such a circumstance, based at least in part on the magnitude of the pushing force applied to the jaw of the user, the jaw may move in the direction of the pushing force in an elevation direction. In various embodiments, the aforementioned application of the engagement force to the jaw engaged with the chin pad may be repeated according to user preference.

vi. Depression

In various embodiments, the passive motion attachment assembly secured to the interchangeable functional attachment interface of the frame assembly may be positioned such that the central axis of the progressive resistance attachment body is at least substantially coplanar about a vertical plane with and at least substantially parallel to a central axis of the horizontal frame arm of the frame assembly. For example, the rotational configuration of the passive motion attachment assembly may be the same in both the elevation configuration and the depression configuration. In various embodiments, the passive motion attachment assembly may be angularly adjusted relative to the horizontal plane such that an end of the passive motion attachment assembly nearest the user moves in a downward direction and the passive motion attachment body extends in both the positive x-direction and the positive y-direction (e.g., relative to the position of the user, as described herein). The passive motion attachment body may extend upward and away from the user in the positive x-direction such that the passive motion attachment body is arranged at between a 45 and 90 degree angle (e.g., an 80 degree angle) relative to the horizontal plane along which it extends when configured in, for example, the protraction configuration, as described herein. In various embodiments, the angular configuration of the passive motion attachment assembly may be such that it accommodates a natural angular motion of the jaw. For example, in various embodiments, the angular configuration of the multi-axis attachment interface hinge may be selectively adjusted such that the passive motion attachment assembly secured thereto may be similarly adjusted to a desired angular position.

As described herein, an elevation attachment may be selectively attached to the passive motion attachment carriage such that an elevation attachment interface thereof extends in a direction toward the user. In various embodiments, said exemplary user may adjust the height of, for example, the vertical frame attachment arm such that the elevation attachment interface disposed on the progressive resistance attachment assembly is aligned and leveled with the mouth of the user. In various embodiments, the elevation attachment may comprise either a single elevation attachment interface or two elevation attachment interfaces, which may correspond to a user exercising only one lateral side of the jaw or both lateral sides of the jaw at a time, respectively.

Once the jaw exercise system is properly configured in the depression configuration described above and aligned with the user, the user may engage the elevation attachment interface. For example, the user may arrange the elevation attachment so as to be at least partially disposed inside the mouth of the user, wherein the elevation attachment interface is engaged with the top surface of the bottom teeth of a user without applying any force thereto.

Upon engaging the elevation attachment, the user may interact with a passive engagement force assembly so as to selectively generate an engagement force to be transmitted to the jaw of the user via the elevation attachment. For example, as described herein, the engagement force may be generated by user interaction with one or more user control interfaces, wherein the user interaction with, for example, one or more knobs, may result in a linear driving force being transmitted to the passive motion attachment carriage (e.g., in a substantially downward direction). In various embodiments, the engagement force generated by said user interaction causes the passive motion attachment carriage, as well as the elevation attachment secured thereto, to move along the passive motion attachment track in a direction corresponding to the direction of the linear driving force. The magnitude of the force generated by the user to be transmitted to the elevation attachment engaged with the jaw of the user may be selectively determined based on a desired jaw range of motion in a depression direction. For example, a user may selectively cause the passive motion attachment carriage to move along the passive motion attachment track, as described herein, in an engagement direction such that a pushing force is applied in the downward direction at the jaw of the user. In such a circumstance, based at least in part on the magnitude of the pushing force applied to the jaw of the user, the jaw may move in the direction of the pushing force in a depression direction. In various embodiments, the aforementioned application of the engagement force to the jaw engaged with the chin pad may be repeated according to user preference.

c. Jaw Motion Force Evaluation

In various embodiments, an exemplary method may be provided for evaluating the jaw movement characteristics of the jaw of a user through a jaw strength characterization exercise. In one exemplary method according to various embodiments, a jaw exercise system, as described herein, may be provided. In various embodiments, as described herein, a user may secure a frame assembly of the jaw exercise system to an effectively immobilized surface or member in an at least substantially stationary position via a stabilizing interface assembly. A user may be positioned so as to face the stabilized frame assembly in a position centered about the central axis of the horizontal frame arm. As described herein, the user may be facing in the positive x-direction with the secured frame assembly positioned directly in front of the user.

In various embodiments, a force characterization attachment assembly, such as, for example, the exemplary embodiment illustrated in FIG. 11, may be securely fastened to an interchangeable functional attachment interface of the frame assembly, as described above. In various embodiments, exemplary methods may be provided for evaluating the jaw movement characteristics through one or more jaw motion force characterization exercises in each of six jaw motion directions.

i. Retraction

In various embodiments, the force characterization attachment assembly secured to the interchangeable functional attachment interface of the frame assembly may be positioned such that the central axis of the force characterization attachment body is at least substantially coplanar about a vertical plane with and at least substantially parallel to a central axis of the horizontal frame arm of the frame assembly. Further, the force characterization attachment assembly may be positioned such that the force characterization attachment sensor is disposed on an opposite end of the force characterization attachment body facing toward the user. As described herein, a retraction attachment may be selectively attached to the force characterization attachment carriage such that a retraction attachment interface thereof extends in a direction toward the user. In various embodiments, said exemplary user may adjust the height of, for example, the vertical frame attachment arm such that the retraction attachment interface disposed on the force characterization attachment assembly is aligned and leveled with the mouth of the user. Once the jaw exercise system is properly configured in the retraction configuration described above and aligned with the user, the user may engage the retraction attachment interface. For example, the user may arrange the retraction attachment so as to be at least partially disposed inside the mouth of the user, wherein the retraction attachment interface is engaged with the inside of the bottom teeth of a user.

Upon engaging the retraction attachment interface, the user may retract the jaw backward in the negative x-direction (e.g., the direction away from the force characterization attachment sensor assembly) so as to generate a pulling force applied at the retraction attachment interface engaged therewith. The force received at the retraction attachment interface may be transmitted to the force characterization attachment carriage via the retraction attachment engaged with the jaw of the user. In such a circumstance, based at least in part on the magnitude of the pulling force received by the retraction attachment, the force characterization attachment carriage may be configured to move along the force characterization attachment track in the direction of the pulling force. For example, in such a circumstance, a component of the force characterization attachment carriage (e.g., the second end of the force characterization attachment carriage user interface mount) may engage the force characterization attachment sensor interface by applying the received pulling force thereto (e.g., via a plunging means, hooked means, and/or the like). Accordingly, the magnitude of the pulling force applied to the force characterization attachment sensor interface in the retraction direction may be determined by the force characterization attachment sensor element, as described herein. In various embodiments, the aforementioned retraction of the jaw engaged with the retraction attachment interface while operably engaged with the force characterization attachment sensor may be repeated according to user preference.

ii. Protraction

In various embodiments, the force characterization attachment assembly secured to the interchangeable functional attachment interface of the frame assembly may be positioned such that the central axis of the force characterization attachment body is at least substantially coplanar about a vertical plane with and at least substantially parallel to a central axis of the horizontal frame arm of the frame assembly. Further, the force characterization attachment assembly may be positioned such that the force characterization attachment sensor is disposed on an opposite end of the force characterization attachment body facing toward the user. For example, the configuration of the force characterization attachment assembly may be the same in both the retraction configuration and the protraction configuration.

As described herein, a protraction attachment may be selectively attached to the force characterization attachment carriage such that a protraction attachment interface thereof extends in a direction toward the user. In various embodiments, said exemplary user may adjust the height of, for example, the vertical frame attachment arm such that the retraction attachment interface disposed on the force characterization attachment assembly is aligned and leveled with the front of the chin of the user. Once the jaw exercise system is properly configured in the protraction configuration described above and aligned with the user, the user may engage the protraction attachment interface. For example, the user may arrange the protraction attachment so as to be physically engaged with the front of the chin of the user so as to establish a substantially flush interface between the chin and the chin pad without transmitting any force therebetween.

Upon engaging the protraction attachment interface, the user may extend the jaw forward in the positive x-direction (e.g., the direction toward the force characterization attachment sensor assembly) so as to generate a pushing force applied at the protraction attachment interface engaged therewith. The force received at the protraction attachment interface may be transmitted to the force characterization attachment carriage via the protraction attachment engaged with the jaw of the user. In such a circumstance, based at least in part on the magnitude of the pushing force received by the protraction attachment, the force characterization attachment carriage may be configured to move along the force characterization attachment track in the direction of the pushing force. For example, in such a circumstance, a component of the force characterization attachment carriage (e.g., the second end of the force characterization attachment carriage user interface mount) may engage the force characterization attachment sensor interface by applying the received pushing force thereto. Accordingly, the magnitude of the pushing force applied to the force characterization attachment sensor interface in the protraction direction may be determined by the force characterization attachment sensor element, as described herein. In various embodiments, the aforementioned protraction of the jaw engaged with the protraction attachment interface while operably engaged with the force characterization attachment sensor may be repeated according to user preference.

iii. Left Lateral Deviation

In various embodiments, the force characterization attachment assembly secured to the interchangeable functional attachment interface of the frame assembly may be positioned such that the central axis of the force characterization attachment body is at least substantially perpendicular to a central axis of the horizontal frame arm of the frame assembly. Further, the force characterization attachment assembly may be positioned such that the force characterization attachment sensor is on a leftward portion of the force characterization attachment body relative to the user. For example, a user may rotate the force characterization attachment assembly 90 degrees counter-clockwise about the central axis of the vertical frame attachment assembly in order to transition from the above-described protraction configuration to a left lateral deviation configuration.

As described herein, a chin pad may be selectively attached to the force characterization attachment carriage and positioned such that the face of the chin pad may be at least substantially perpendicular to the central axis of the force characterization attachment body and may be facing away from the force characterization attachment sensor (e.g., facing in the same direction in which the force characterization attachment sensor is facing). In various embodiments, the exemplary user may adjust the height of, for example, the vertical frame attachment arm such that the chin pad disposed on the force characterization attachment assembly is aligned and leveled with the left side of the chin of the user. Once the jaw exercise system is properly configured in the left lateral deviation configuration described above and aligned with the user, the user may engage the chin pad. For example, the user may arrange the chin pad so as to be physically engaged with the left side of the chin of the user as to establish a substantially flush interface between the chin and the chin pad without transmitting any force therebetween.

Upon engaging the chin pad, the user may move the jaw laterally in the leftward direction (e.g., the direction toward the force characterization attachment sensor assembly) so as to generate a pushing force applied at the chin pad engaged therewith. The force received at the chin pad may be transmitted to the force characterization attachment carriage via the chin pad engaged with the jaw of the user. In such a circumstance, based at least in part on the magnitude of the pushing force received by the chin pad, the force characterization attachment carriage may be configured to move along the force characterization attachment track in the direction of the pushing force. For example, in such a circumstance, a component of the force characterization attachment carriage (e.g., the second end of the force characterization attachment carriage user interface mount) may engage the force characterization attachment sensor interface by applying the received pushing force thereto. Accordingly, the magnitude of the pushing force applied to the force characterization attachment sensor interface in the left lateral deviation direction may be determined by the force characterization attachment sensor element, as described herein. In various embodiments, the aforementioned lateral movement of the jaw engaged with the chin pad while operably engaged with the force characterization attachment sensor may be repeated according to user preference.

iv. Right Lateral Deviation

In various embodiments, the force characterization attachment assembly secured to the interchangeable functional attachment interface of the frame assembly may be positioned such that the central axis of the force characterization attachment body is at least substantially perpendicular to a central axis of the horizontal frame arm of the frame assembly. Further, the force characterization attachment assembly may be positioned such that the force characterization attachment sensor is on a rightward portion of the force characterization attachment body relative to the user. For example, a user may rotate the force characterization attachment assembly 180 degrees about the central axis of the vertical frame attachment assembly in order to transition from the above-described left lateral deviation configuration to a right lateral deviation configuration.

As described herein, a chin pad may be selectively attached to the force characterization attachment carriage and positioned such that the face of the chin pad may be at least substantially perpendicular to the central axis of the force characterization attachment body and may be facing away from the force characterization attachment sensor (e.g., facing in the same direction in which the force characterization attachment sensor is facing). In various embodiments, the exemplary user may adjust the height of, for example, the vertical frame attachment arm such that the chin pad disposed on the force characterization attachment assembly is aligned and leveled with the right side of the chin of the user. Once the jaw exercise system is properly configured in the right lateral deviation configuration described above and aligned with the user, the user may engage the chin pad. For example, the user may arrange the chin pad so as to be physically engaged with the right side of the chin of the user so as to establish a substantially flush interface between the chin and the chin pad without transmitting any force therebetween.

Upon engaging the chin pad, the user may move the jaw laterally in the rightward direction (e.g., the direction toward the force characterization attachment sensor assembly) so as to generate a pushing force applied at the chin pad engaged therewith. The force received at the chin pad may be transmitted to the force characterization attachment carriage via the chin pad engaged with the jaw of the user. In such a circumstance, based at least in part on the magnitude of the pushing force received by the chin pad, the force characterization attachment carriage may be configured to move along the force characterization attachment track in the direction of the pushing force. For example, in such a circumstance, a component of the force characterization attachment carriage (e.g., the second end of the force characterization attachment carriage user interface mount) may engage the force characterization attachment sensor interface by applying the received pushing force thereto. Accordingly, the magnitude of the pushing force applied to the force characterization attachment sensor interface in the right lateral deviation direction may be determined by the force characterization attachment sensor element, as described herein. In various embodiments, the aforementioned lateral movement of the jaw engaged with the chin pad while operably engaged with the force characterization attachment sensor may be repeated according to user preference.

v. Elevation

In various embodiments, the force characterization attachment assembly secured to the interchangeable functional attachment interface of the frame assembly may be positioned such that the central axis of the force characterization attachment body is at least substantially coplanar about a vertical plane with and at least substantially parallel to a central axis of the horizontal frame arm of the frame assembly. The force characterization attachment assembly may be positioned such that the force characterization attachment sensor is disposed on an opposite end of the force characterization attachment body facing toward the user. For example, a user may rotate the force characterization attachment assembly 90 degrees counter-clockwise about the central axis of the vertical frame attachment assembly in order to transition from the above-described right lateral deviation configuration to an intermediate configuration that may enable a user to further configure the force characterization assembly attachment in an elevation configuration. As described herein, the force characterization attachment assembly may be angularly adjusted relative to the horizontal plane such that an end of the force characterization attachment assembly nearest the user (e.g., the end of the force characterization attachment assembly opposite the force characterization attachment sensor assembly) moves in a downward direction and the force characterization attachment body extends in both the positive x-direction and the positive y-direction (e.g., relative to the position of the user, as described herein). The force characterization attachment body may extend upward and away from the user in the positive x-direction such that the force characterization attachment body is arranged at between a 45 and 90 degree angle (e.g., a 70 degree angle) relative to the horizontal plane along which it extends when configured in, for example, the protraction configuration, as described herein. In various embodiments, the angular configuration of the force characterization attachment assembly may be such that it accommodates a natural angular motion of the jaw. For example, in various embodiments, the angular configuration of the multi-axis attachment interface hinge may be selectively adjusted such that the force characterization attachment assembly secured thereto may be similarly adjusted to a desired angular position.

As described herein, an elevation attachment may be selectively attached to the force characterization attachment carriage such that an elevation attachment interface thereof extends in a direction toward the user. In various embodiments, said exemplary user may adjust the height of, for example, the vertical frame attachment arm such that the elevation attachment interface disposed on the force characterization attachment assembly is aligned and leveled with the mouth of the user. In various embodiments, the elevation attachment may comprise either a single elevation attachment interface or two elevation attachment interfaces, which may correspond to a user exercising only one lateral side of the jaw or both lateral sides of the jaw at a time, respectively.

Once the jaw exercise system is properly configured in the elevation configuration described above and aligned with the user, the user may engage the elevation attachment interface. For example, the user may arrange the elevation attachment so as to be at least partially disposed inside the mouth of the user, wherein the elevation attachment interface is engaged with the top surface of the bottom teeth of a user without transmitting any force therebetween.

Upon engaging the elevation attachment interface, the user may extend the jaw in a substantially upward direction (e.g., the direction toward the force characterization attachment sensor assembly) so as to generate a pushing force applied at the elevation attachment interface engaged therewith. The force received at the elevation attachment interface may be transmitted to the force characterization attachment carriage via the elevation attachment engaged with the jaw of the user. In such a circumstance, based at least in part on the magnitude of the pushing force received by the elevation attachment, the force characterization attachment carriage may be configured to move along the force characterization attachment track in the direction of the pushing force. For example, in such a circumstance, a component of the force characterization attachment carriage (e.g., the second end of the force characterization attachment carriage user interface mount) may engage the force characterization attachment sensor interface by applying the received pushing force thereto. Accordingly, the magnitude of the pushing force applied to the force characterization attachment sensor interface in the elevation direction may be determined by the force characterization attachment sensor element, as described herein. In various embodiments, the aforementioned elevation of the jaw engaged with the elevation attachment interface while operably engaged with the force characterization attachment sensor may be repeated according to user preference.

vi. Depression

In various embodiments, the force characterization attachment assembly secured to the interchangeable functional attachment interface of the frame assembly may be positioned such that the central axis of the force characterization attachment body is at least substantially coplanar about a vertical plane with and at least substantially parallel to a central axis of the horizontal frame arm of the frame assembly. The force characterization attachment assembly may be positioned such that that force characterization attachment sensor is disposed on an end of the force characterization attachment body nearest the user and facing away from the user. For example, a user may rotate the force characterization attachment assembly 180 degrees about the central axis of the vertical frame attachment assembly in order to transition from the above-described elevation configuration to an intermediate configuration that may enable a user to further configure the force characterization assembly attachment in a depression configuration. As described herein, the force characterization attachment assembly may be angularly adjusted relative to the horizontal plane such that an end of the force characterization attachment assembly nearest the user (e.g., the end of the force characterization attachment assembly at which the force characterization attachment sensor is disposed) moves in a downward direction and the force characterization attachment body extends in both the positive x-direction and the positive y-direction (e.g., relative to the position of the user, as described herein). The force characterization attachment body may extend upward and away from the user in the positive x-direction such that the force characterization attachment body is arranged at between a 45 and 90 degree angle (e.g., an 80 degree angle) relative to the horizontal plane along which it extends when configured in, for example, the protraction configuration, as described herein. In various embodiments, the angular configuration of the force characterization attachment assembly may be such that it accommodates a natural angular motion of the jaw. For example, in various embodiments, the angular configuration of the multi-axis attachment interface hinge may be selectively adjusted such that the force characterization attachment assembly secured thereto may be similarly adjusted to a desired angular position.

As described herein, a chin pad may be selectively attached to the force characterization attachment carriage and positioned such that the face of the chin pad may be at least substantially perpendicular to the central axis of the force characterization attachment body. In various embodiments, the exemplary user may adjust the height of, for example, the vertical frame attachment arm such that the chin pad disposed on the force characterization attachment assembly is aligned and leveled with the bottom of the chin of the user. Once the jaw exercise system is properly configured in the depression configuration described above and aligned with the user, the user may engage the chin pad. For example, the user may arrange the chin pad so as to as to establish a substantially flush interface between the bottom of the chin and the chin pad without transmitting any force therebetween.

Upon engaging the chin pad, the user may open the jaw in a substantially downward direction (e.g., the direction toward the force characterization attachment sensor assembly) so as to generate a pushing force applied at the chin pad engaged therewith. The force received at the chin pad may be transmitted to the force characterization attachment carriage via the chin pad engaged with the jaw of the user. In such a circumstance, based at least in part on the magnitude of the pushing force received by the chin pad, the force characterization attachment carriage may be configured to move along the force characterization attachment track in the direction of the pushing force. For example, in such a circumstance, a component of the force characterization attachment carriage (e.g., the second end of the force characterization attachment carriage user interface mount) may engage the force characterization attachment sensor interface by applying the received pushing force thereto. Accordingly, the magnitude of the pushing force applied to the force characterization attachment sensor interface in the depression direction may be determined by the force characterization attachment sensor element, as described herein. In various embodiments, the aforementioned depression of the jaw engaged with the chin pad while operably engaged with the force characterization attachment sensor may be repeated according to user preference.

d. Hyoid Motion Jaw Evaluation

In various embodiments, an exemplary method may be provided for evaluating the jaw movement characteristics of the jaw of a user through a hyoid motion exercise. In various embodiments, a jaw exercise system, as described herein, may be provided. In various embodiments, as described herein, a user may secure a frame assembly of the jaw exercise system to an effectively immobilized surface or member in an at least substantially stationary position via a stabilizing interface assembly. A user may be positioned so as to face the stabilized frame assembly in a position centered about the central axis of the horizontal frame arm. As described herein, the user may be facing in the positive x-direction with the secured frame assembly positioned directly in front of the user.

In various embodiments, a hyoid motion attachment assembly, such as, for example, the exemplary embodiment illustrated in FIG. 12, may be securely fastened to an interchangeable functional attachment interface of the frame assembly, as described above. In various embodiments, exemplary methods may be provided for evaluating the jaw movement characteristics, such as, for example, characterizing the range of motion of various muscles associated with the hyoid bone of a user, through one or more jaw motion force characterization exercises in each of four motion directions. As described herein, a user may evaluate various jaw-related muscles, such as, for example, various muscles attached to a hyoid of a user via interaction with the hyoid motion attachment assembly, which may encourage user activation of the hyoid and measure the range of motion of the muscles associated therewith.

In various embodiments, the hyoid motion attachment assembly secured to the interchangeable functional attachment interface of the frame assembly may be positioned such that the central axis of the hyoid motion attachment body is at least substantially coplanar about a vertical plane with and at least substantially parallel to a central axis of the horizontal frame arm of the frame assembly. The hyoid motion attachment assembly may be positioned such that that hyoid motion attachment window is disposed on an end of the hyoid motion attachment body nearest the user. For example, a user may place the jaw (e.g., the bottom of the chin) upon the upper surface of the hyoid motion attachment window such that at least a portion of a front neck region of the user may be positioned below the upper surface and may face in a direction that is at least substantially parallel to the central axis of the hyoid motion attachment body and at least substantially perpendicular to a hyoid motion attachment indicator display surface disposed at an end of the hyoid motion attachment body opposite the hyoid motion attachment window. Further, the user may secure a hyoid motion indicator device (e.g., a laser pointer), as described herein, to at least a portion of the front neck region of the user such that a hyoid motion indicator, such as, for example, a laser, a beam of light, and/or the like, projecting in a linear direction away from the user may be projected through the hyoid motion attachment window and onto a hyoid motion attachment indicator display surface disposed at an end of the hyoid motion attachment body furthest from the user.

In various embodiments, as described herein, the user may effectively move the hyoid motion indicator about the hyoid motion attachment indicator display surface by stimulating (e.g., moving) the aforementioned muscles corresponding to the hyoid bone so as to at least partially activate the hyoid bone. For example, a user may evaluate the above-referenced jaw-related muscles using the movement of the at least a portion of the front neck region of the user and the resulting displacement of the hyoid motion indicator on the hyoid motion attachment indicator display surface to encourage user activation of the hyoid bone and measuring the range of motion of the corresponding muscles.

III. CONCLUSION

Many modifications and other embodiments will come to mind to one skilled in the art to which this disclosure pertains having the benefit of the teachings presented in the foregoing descriptions and the associated drawings. Therefore, it is to be understood that the disclosure is not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed:

1. A system for evaluating jaw movement characteristics of a user, said user having a jaw, the jaw of the user comprising one or more body parts of a user that are at least substantially functionally attached to said jaw, said system comprising:
    a frame assembly, the frame assembly comprising:
        an interchangeable assembly interface; and
        a stabilizing interface assembly configured to operably secure the frame assembly in an at least substantially stationary position;
    at least one interchangeable assembly configured to attach to the interchangeable assembly interface of the frame assembly, the at least one interchangeable assembly comprising a plurality of user interface attachments configured to interact with the jaw of the user;
    wherein the at least one interchangeable assembly further comprises a hexadirectional range of motion such that the respective plurality of user interface attachments of the at least one interchangeable assembly is configured to facilitate the evaluation of a jaw movement characteristic of the user in at least one of six jaw motion directions.

2. The system of claim 1, wherein the at least one of the six jaw motion directions comprises one or more of a retraction direction, a protraction direction, a left lateral deviation direction, a right lateral deviation direction, an elevation direction and a depression direction.

3. The system of claim 1, wherein the at least one interchangeable assembly comprises a progressive resistance attachment assembly, the progressive resistance attachment assembly comprising:
    a plurality of user interface attachments configured to interact with the jaw of the user; and
    a resistance force assembly configured to provide a resistance force in a resistance direction, a directional configuration of the resistance direction being based on a user configuration of the progressive resistance attachment assembly;
    wherein each of the plurality of user interface attachments of the progressive resistance attachment assembly is configured to receive a force from the jaw of the user in at least one of the six jaw motion directions, the progressive resistance attachment assembly being configurable such that each of the six jaw motion directions are substantially opposite a resistance direction; and
    wherein the six jaw motion directions define a hexadirectional range of motion of the progressive resistance attachment assembly, such that the system is configured to evaluate a jaw movement characteristic of the user in each of the six jaw motion directions.

4. The system of claim 3, wherein the resistance force assembly comprises a pulley device.

5. The system of claim 4, wherein the resistance force assembly comprises two pulley devices.

6. The system of claim 1, wherein the at least one interchangeable assembly comprises a passive motion attachment assembly, the passive motion attachment assembly comprising:
    a plurality of user interface attachments configured to interact with the jaw of the user; and
    a passive engagement force assembly configured to provide an engagement force in an engagement direction, a directional configuration of the engagement direction being based on a user configuration of the passive motion attachment assembly;
    wherein each of the plurality of user interface attachments of the passive motion attachment assembly is configured to apply an engagement force to the jaw of the user in at least one of six jaw motion directions, the passive motion attachment assembly being configurable such that each of the six jaw motion directions are substantially similar to an engagement direction.

7. The system of claim 6, wherein the passive engagement force assembly comprises one or more user control interfaces configured to receive a force applied thereto, the passive engagement force assembly being further configured to transmit the force to at least one portion of the passive motion attachment assembly in an engagement direction.

8. The system of claim 6, wherein the passive engagement force assembly is configured to electronically generate the engagement force.

9. The system of claim 1, wherein the at least one interchangeable assembly comprises a force characterization attachment assembly configured to attach to the interchangeable assembly interface of the frame assembly, the force characterization attachment assembly comprising:
a plurality of user interface attachments configured to receive an applied force transmitted from the user in an applied force direction; the force characterization attachment assembly being configurable such that at least one of six jaw motion directions are substantially similar to an applied force direction; and
a force characterization attachment sensor assembly configured to interact with the at least one of the plurality of user interface attachments so as to receive the applied force and measure the magnitude of the applied force in an applied force direction.

10. The system of claim 1, further comprising a hyoid motion attachment assembly configured to attach to the interchangeable assembly interface of the frame assembly and facilitate the evaluation of one or more jaw-related muscles by encouraging user activation thereof and measuring a range of motion of the one or more jaw-related muscles.

11. The system of claim 10, wherein the one or more jaw-related muscles comprise muscles attached to the hyoid bone of the user.

12. The system of claim 1, wherein the frame assembly further comprises a multi-axis attachment interface hinge connected to the interchangeable assembly interface, the multi-axis attachment interface hinge comprising an angular range of motion about a first axis, wherein the multi-axis attachment interface hinge is configured to enable an adjustment of an angular configuration of the interchangeable assembly attached to the interchangeable assembly interface about the first axis.

13. The system of claim 12, wherein the first axis comprises a horizontal axis so as to enable the adjustment of the angular configuration of an interchangeable assembly within a vertical plane, wherein the angular configuration of the of the interchangeable assembly is such that at least one of the six jaw motion directions corresponds to a natural angular motion of the jaw of the user.

14. The system of claim 12, wherein the multi-axis attachment interface hinge further comprises an angular range of motion about a second axis, wherein the multi-axis attachment interface hinge is further configured to enable an adjustment of an angular configuration of the interchangeable assembly attached to the interchangeable assembly interface about the second axis.

15. The system of claim 1, further comprising at least one user stabilization features configured to provide a stationary support for the user such that the user may limit movement of the user as being exclusively movement of the jaw of the user.

16. The system of claim 1, wherein the frame assembly is configured such that an interchangeable assembly configured to attach to the interchangeable assembly interface may be adjustable along both a vertical axis and horizontal axis.

17. A method for evaluating jaw movement characteristics of a user, said user having a jaw, the jaw of the user comprising one or more body parts of a user that are at least substantially functionally attached to said jaw, said method comprising:
providing a jaw exercise system comprising:
a frame assembly, the frame assembly comprising:
an interchangeable assembly interface; and
a stabilizing interface assembly configured to operably secure the frame assembly in an at least substantially stationary position;
at least one interchangeable assembly configured to attach to the interchangeable assembly interface of the frame assembly, the at least one interchangeable assembly comprising a plurality of user interface attachments configured to interact with the jaw of the user;
wherein the at least one interchangeable assembly further comprises a hexadirectional range of motion such that the respective plurality of user interface attachments of the at least one interchangeable assembly is configured to facilitate the evaluation of a jaw movement characteristic of the user in at least one of six jaw motion directions; and
interacting with the at least one interchangeable assembly to evaluate a jaw movement characteristic of the user in the at least one of six jaw motion directions.

18. The method of claim 17, wherein the at least one interchangeable assembly comprises a progressive resistance attachment assembly; and wherein interacting with the at least one interchangeable assembly to evaluate the jaw movement characteristic of the user in the at least one of six jaw motion directions comprises executing at least one active range of motion exercise.

19. The method of claim 17, wherein the at least one interchangeable assembly comprises a passive motion attachment assembly; and wherein interacting with the at least one interchangeable assembly to evaluate the jaw movement characteristic of the user in the at least one of six jaw motion directions comprises executing at least one passive range of motion exercise.

20. The method of claim 17, wherein the at least one interchangeable assembly comprises a force characterization attachment assembly; and wherein interacting with the at least one interchangeable assembly to evaluate the jaw movement characteristic of the user in the at least one of six jaw motion directions comprises executing jaw force characterization exercise.

* * * * *